United States Patent

Volkmann et al.

[11] Patent Number: 5,854,232
[45] Date of Patent: Dec. 29, 1998

[54] ACYCLIC ANC CYCLIC AMIDES AS NEUROTRANSMITTER RELEASE ENHANCERS

[75] Inventors: Robert A. Volkmann, Mystic; Vytautas J Jasys, Griswold; Gene M Bright, Groton; Anabella Villalobos, Niantic; Patricia A Seymour, Uncasville, all of Conn.

[73] Assignee: Pfizer Inc., New York, N.Y.

[21] Appl. No.: 737,376

[22] PCT Filed: Mar. 20, 1995

[86] PCT No.: PCT/IB95/00189

§ 371 Date: Feb. 19, 1997

§ 102(e) Date: Feb. 19, 1997

[87] PCT Pub. No.: WO95/29909

PCT Pub. Date: Nov. 9, 1995

[51] Int. Cl.⁶ .................. C07D 401/06; C07D 239/26; A61K 31/44; A61K 31/415
[52] U.S. Cl. .............. 514/210; 514/247; 514/252; 514/256; 514/332; 514/340; 514/341; 514/357; 514/359; 514/378; 514/383; 514/386; 514/406; 514/430; 514/461; 540/356; 544/224; 544/242; 546/255; 546/272.7; 546/276.4; 546/336
[58] Field of Search .................. 514/357, 210, 514/247, 252, 250, 332, 340, 341, 359, 378, 383, 386, 406, 430, 461; 340/356; 544/224, 242; 546/336, 255, 272.7, 276.4; 548/240, 255, 262.2, 316.4, 356.1, 543; 549/13, 991

[56] References Cited

U.S. PATENT DOCUMENTS 4,216,318   8/1980   Brown et al. ................ 544/310

FOREIGN PATENT DOCUMENTS 0403159   6/1990   European Pat. Off. ........... 546/334

Primary Examiner—Zinna Northington Davis
Attorney, Agent, or Firm—Peter C. Richardson; Paul H. Ginsburg; B. Timothy Creagan

[57] ABSTRACT

This invention relates to compounds of formula (IA), (IB), (IC) or (ID), wherein m, X, Z, $R^2$, $R^3$, $R^4$, $R^5$, $R^6$, $R^{14}$ and the dotted lines are as defined below, their pharmaceutically acceptable salts, pharmaceutical compositions containing them and methods of using them to treat Alzheimer's disease, age-associated memory impairment, Parkinson's disease and other central nervous system disorders. The claimed compounds have the ability to enhance the release of neurotransmitters such as acetylcholine, dopamine and serotonin.

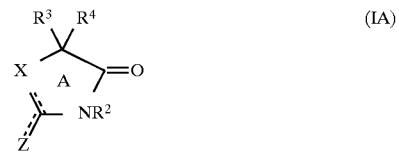

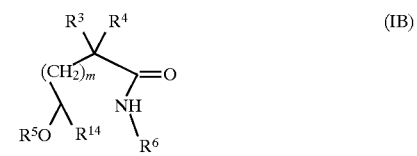

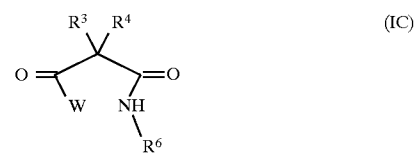

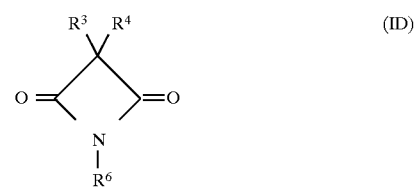

43 Claims, No Drawings

ACYCLIC ANC CYCLIC AMIDES AS NEUROTRANSMITTER RELEASE ENHANCERS

This application is a 371 of PCT/IB95/00189 filed Mar. 20, 1995.

This invention relates to novel substituted heterocyclic compounds, their pharmaceutically acceptable salts, pharmaceutical compositions containing them and methods of using them to treat Alzheimer's disease, age associated memory impairment, Parkinson's disease and other central nervous system disorders such as mental retardation, developmental disorders, disruptive behavioral disorders, organic mental disorders (including dementia and psychoactive substance induced organic mental disorders), psychoactive substance abuse disorders, mood disorders, anxiety disorders, somatoform disorders, dissociative disorders, attention deficit disorder, schizophrenia and personality disorders. The claimed compounds have the ability to enhance the release of neurotransmitters such as acetylcholine, dopamine and serotonin.

World Patent Application WO 93/14085, which was published on Jul. 22, 1993, refers to certain indole derivatives as having the ability to enhance the release of acetylcholine. The ability of similar compounds to enhance the release of acetylcholine is referred to by Wilkerson et al., *J. Med. Chem.*, 36, 2899–2907 (1993), Smith et al., *Drug Development Research*, 29, 262–270 (1993), and Zaczek et al., *Curr. Opin. Invest. Drugs*, 2 (10), 1097–1104 (1993).

Substituted polycyclic compounds that enhance acetylcholine release are referred to in U.S. Pat. No. 5,278,162, which issued on Jan. 11, 1994 and World Patent Application WO 93/14092, which was published on Jul. 22, 1993.

SUMMARY OF THE INVENTION

This invention relates to compounds of the formula

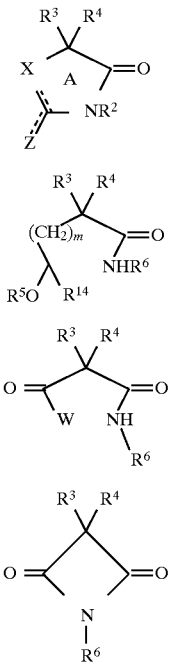

wherein both dotted lines represent optional double bonds;

m is an integer from zero to four;

Z is oxygen or sulfur when it is double bonded to ring A and Z is hydroxy, $(C_1-C_{10})$ alkyl—S—, adamant—2—yl—S—, benzyl—S—, phenyl—C(=O)CH$_2$—S—, $(C_1-C_6)$ alkyl—O—C(=O)—CH$_2$—S— or (H,H) (L, Z represents two hydrogen atoms, each of which is single bonded to the same carbon of ring A) when Z is single bonded to ring A;

X is CH$_2$CH$_2$, NR$^1$, CHR$^1$ or a direct link between the carbon to which Z is attached and the carbon to which R$^3$ and R$^4$ are attached;

R$^1$ is hydrogen, $(C_1-C_6)$alkyl or $(C_1-C_6)$alkylphenyl when ring A is saturated (i.e., when ring A contains no double bonds) and R$^1$ is absent when ring A contains a double bond;

R$^2$ and R$^6$ are independently selected from naphthyl, phenyl, $(C_1-C_6)$alkylphenyl, 1-adamantyl, 2-adamantyl, $(C_1-C_8)$ straight or branched alkyl, $(C_3-C_{10})$ cycloalkyl and $(C_8-C_{30})$bicyclic or tricyclic alkyl; wherein said $(C_3-C_{10})$ cycloalkyl and said $(C_8-C_{30})$ bicyclic or tricyclic alkyl may optionally be substituted with a hydroxy group; and 5 wherein said adamantyl groups may optionally be substituted with from one to three substituents independently selected from $(C_1-C_6)$alkyl, halo and hydroxy;

R$^3$ and R$^4$ are independently selected from benzyl, wherein the phenyl moiety of said benzyl may optionally be substituted with an amino or nitro group; hydrogen, phenyl, (N≡C)-$(C_1-C_6)$alkyl, $(C_1-C_6)$alkyl—O—C(=O)—$(C_1-C_6)$ alkyl and Het-CH$_2$, wherein Het is selected from 2-, 3- or 4-pyridinyl, furyl, tetrahydrofuryl, pyrimidyl, pyrazinyl, pyrazolyl, isoxazolyl, thiophenyl and triazolyl;

R$^5$ is hydrogen, phenyl-$(C_1-C_6)$alkyl, $(C_1-C_{10})$alkyl or $(C_1-C_6)$alkyl—C(=O)—;

W is hydrogen, OR$^7$, hydroxy, R$^{11}$ or NR$^{12}$R$^{13}$;

each of R$^7$ and R$^{11}$ is independently selected from $(C_1-C_6)$alkyl;

each of R$^{12}$ and R$^{13}$ is independently selected from $(C_1-C_3)$alkyl; and R$^{14}$ is hydrogen, $(C_1-C_4)$alkyl, benzyl or phenyl;

with the proviso that (a) no more than one of the two dotted lines in formula IA can represent a double bond in any one compound, (b) when Z is (H, H), X is CH$_2$ or CH$_2$CH$_2$, (c) when Z is oxygen or (H, H) and X is CHR$^1$, R$^1$ must be hydrogen, (d) when Z is sulfur and X is NR$^1$, R$^1$ must be hydrogen, and (e) one of R$^3$ and R$^4$ must be Het-CH$_2$.

The compounds of formulae IA, IB, IC and ID that are basic in nature are capable of forming a wide variety of salts with various inorganic and organic acids. The acids that may be used to prepare pharmaceutically acceptable acid addition salts of those compounds of formula I that are basic in nature are those that form non-toxic acid addition salts, i.e., salts containing pharmacologically acceptable anions, such as the hydrochloride, hydrobromide, hydroiodide, nitrate, sulfate, bisulfate, phosphate, acid phosphate, isonicotinate, acetate, lactate, salicylate, citrate, acid citrate, tartrate, pantothenate, bitartrate, ascorbate, succinate, maleate, gentisinate, fumarate, gluconate, glucaronate, saccharate, formate, benzoate, glutamate, methanesulfonate, ethanesulfonate, benzenesulfonate, p-toluenesulfonate and pamoate [i.e., 1,1'-methylene-bis-(2-hydroxy-3-naphthoate)] salts.

This invention also relates to the pharmaceutically acceptable acid addition salts of compounds of the formulae IA, IB, IC and ID.

The term "alkyl", as used herein, unless otherwise indicated, includes saturated monovalent hydrocarbon radicals having straight, branched or cyclic moieties or combinations thereof.

Preferred compounds of this invention include compounds of the formulae IA, IB, IC and ID wherein one of R$^3$ and R$^4$ is 2-, 3- or 4-pyridinylmethyl.

Other preferred compounds of this invention include compounds of the formulae IA, IB, IC and ID wherein one of $R^3$ and $R^4$ is 2-, 3- or 4-pyridinylmethyl, the other is Het-$CH_2$, and $R^2$ or $R^6$ is 1-adamantyl, 2-adamantyl or cyclooctyl.

Other preferred compounds of this invention include compounds of the formula IA, wherein X is $CH_2$, Z is oxygen and $R^2$ is 1- or 2-adamantyl or cyclooctyl.

Other preferred compounds of this invention include compounds of the formula IA, wherein $R^2$ is 1 - or 2-adamantyl and compounds of the formula IB wherein $R^6$ is 1 -or 2-adamantyl or cyclooctyl.

Other preferred compounds of this invention include compounds of the formula IA, wherein Z is (H,H) and X is $CH_2$.

Other preferred compounds of this invention include compounds of the formula IC wherein $R^{14}$ is hydrogen or $(C_1-C_4)$alkyl.

Other preferred compounds of this invention include: (a) compounds of the formula IA wherein $R^3$ and $R^4$ are independently selected from 2-, 3- or 4-pyridinylmethyl, $R^2$ is 1- or 2-adamantyl, Z is oxygen and X is $CH_2$; and (b) compounds of the formula IA wherein $R^3$ and $R^4$ are independently selected from 2-, 3- or 4-pyridinylmethyl, $R^2$ is cyclooctyl, Z is oxygen and X is $CH_2$.

Other embodiments of this invention include:

(a) compounds of the formula IA wherein X is $CH_2$, $CH_2CH_2$ or $NR^1$;

(b) compounds of the formula IA wherein X is a direct link between the carbon to which Z is attached and the carbon to which $R^3$ and $R^4$ is attached, and Z is (H, H) or oxygen;

(c) compounds of the formula IA wherein X is NH;

(d) compounds of the formula IA wherein X is $CH_2$;

(e) compounds of the formula IA wherein Z is oxygen;

(f) compounds of the formula IB wherein $R^5$ is hydrogen;

(g) compounds of the formula IA or IB wherein $R^2$ or $R^6$, respectively, is 1-or 2-adamantyl;

(h) compounds of the formula IA or IB wherein $R^2$ or $R^6$, respectively, is $(C_5-C_{10})$ cycloalkyl;

(i) compounds of the formula IB wherein $R^5$ is $(C_1-C_3)$ alkyl;

(j) compounds of the formula IB wherein $R^5$ is $(C_1-C_3)$ alkyl—C(=O)—;

(k) compounds of the formula IA wherein X is $NR^1$ and Z is oxygen;

(l) compounds of the formula IA wherein X is NH and Z is sulfur;

(m) compounds of the formula IA wherein X is $CH_2CH_2$, $NR^1$ or $CHR^1$;

(n) compounds of the formula IA wherein X is $CHR^1$ and $R^1$ is other than $(C_1-C_6)$ alkylphenyl;

(o) compounds of the formula IC wherein $R^3$ and $R^4$ are independently selected from 2-, 3- or 4-pyridinylmethyl;

(p) compounds of the formula IC wherein W is methyl and $R^6$ is 1-adamantyl;

(q) compounds of the formula IC wherein $R^6$ is 1- or 2-adamantyl;

(r) compounds of the formula ID wherein $R^6$ is 1- or 2-adamantyl;

(s) compounds of the formula IC wherein W is $(C_1-C_4)$ alkyl;

(t) compounds of the formula IC wherein W is $OR^7$;

(u) compounds of the formula IC wherein W is hydroxy;

(v) compounds of the formula IC wherein W is a substituted amino group;

(w) compounds of the formula IB wherein $R^{14}$ is hydrogen;

(x) compounds of the formula IB wherein $R^{14}$ is $(C_1-C_6)$ alkyl;

(y) compounds of the formula ID wherein $R^6$ is $(C_3-C_{10})$ cycloalkyl or $(C_8-C_{30})$ bicyclic or tricyclic alkyl; and (z) compounds of the formula IC wherein one or both of $R^3$ and $R^4$ are selected from 2-, 3- and 4-pyridinylmethyl.

This invention also relates to compounds of the formula

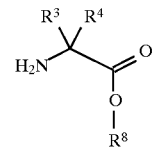

II wherein $R^3$ and $R^4$ are defined as above for compounds of the formulae IA and IB and $R^8$ is $(C_1-C_{10})$alkyl. These compounds are useful as intermediates in the synthesis of compounds of the formula IA.

Examples of compounds of the formula II include such compounds wherein: (a) $R^8$ is methyl and $R^3$ and $R^4$ are independently selected from 2-, 3- and 4-pyridinylmethyl; (b) $R^8$ is $(C_1-C_3)$alkyl and $R^3$ and $R^4$ are independently selected from 2-, 3- and 4-pyridinylmethyl; and (c) one of $R^3$ and $R^4$ is 2-, 3- or 4-pyridinylmethyl and the other is Het-$CH_2$, wherein Het is defined as above for compounds of the formulae IA and IB, and $R^8$ is $(C_1-C_3)$alkyl.

This invention also relates to compounds of the formula

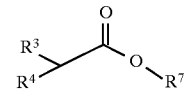

X wherein $R^7$ is $(C_1-C_6)$alkyl and $R^3$ and $R^4$ are defined as above for compounds of the formulae IA and IB. These compounds are useful as intermediates in the synthesis of compounds of the formulae IA, IB, IC and ID. Examples of compounds of the formula X include such compounds wherein: (a) $R^3$ and $R^4$ are independently selected from 2-, 3- or 4-pyridinylmethyl and $R^7$ is methyl; (b) one of $R^3$ and $R^4$ is 4-pyridylmethyl and $R^7$ is $(C_1-C_3)$alkyl, and (c) one of $R^3$ and $R^4$ is 4-pyridinylmethyl and the other is Het-$CH_2$, wherein Het is defined as above for compounds of the formulae IA and IB, and $R^7$ is $(C_1-C_3)$alkyl.

The compounds of formulae IA, IB, IC, ID, II and X above may contain chiral centers and therefore may exist in different enantiomeric forms. This invention relates to all optical isomers and all other stereoisomers of compounds of the formulae IA, IB, IC, ID, II and X and mixtures thereof.

Formulae IA, IB, IC, ID, II and X above also include compounds identical to those depicted but for the fact that one or more hydrogens or carbon atoms are replaced by isotopes thereof. Such compounds are useful as research and diagnostic tools in metabolism pharmacokinetics studies and in binding assays.

This invention also relates to a pharmaceutical composition for treating Alzheimer's disease, age associated memory impairment or Parkinson's disease in a human, comprising an amount of a compound of the formula IA, IB, IC or ID, or pharmaceutically acceptable salt thereof, that is effective in treating or preventing such condition, and a pharmaceutical acceptable carrier.

The present invention also relates to a method of treating Alzheimer's disease, age associated memory impairment or Parkinson's disease in a human, comprising administering to said human an amount of a compound of the formula IA, IB, IC or ID, or pharmaceutically acceptable salt thereof, that is effective in treating or preventing such condition.

The present invention also relates to a pharmaceutical composition for treating Alzheimer's disease, age associated memory impairment or Parkinson's disease in a human, comprising an acetylcholine, dopamine or serotonin release enhancing effective amount of a compound of the formula IA, IB, IC or ID, or a pharmaceutical acceptable salt thereof, and a pharmaceutically acceptable carrier.

The present invention also relates to a method of treating Alzheimer's disease, age associated memory impairment or Parkinson's disease in a human, comprising an administering to said human an acetylcholine, dopamine or serotonin release enhancing effective amount of a compound of the formula IA, IB, IC or ID, or pharmaceutically acceptable salt thereof.

This invention also relates to a pharmaceutical composition for treating a condition selected from mental retardation, developmental disorders, disruptive behavioral disorders, organic mental disorders (including dementia and psychoactive substance induced organic mental disorders), psychoactive substance abuse disorders, mood disorders, anxiety disorders, somatoform disorders, dissociative disorders, attention deficit disorder, schizophrenia and personality disorders in a human, comprising an amount of a compound of the formula IA, IB, IC or ID, or pharmaceutically acceptable salt thereof, that is effective in treating or preventing such condition, and a pharmaceutical acceptable carrier.

The present invention also relates to a method of treating a condition selected from mental retardation, developmental disorders, disruptive behavioral disorders, organic mental disorders (including dementia and psychoactive substance induced organic mental disorders), organic mental disorders, psychoactive substance abuse disorders, mood disorders, anxiety disorders, somatoform disorders, dissociative disorders, attention deficit disorder, schizophrenia and personality disorders in a human, comprising administering to said human an amount of a compound of the formula IA, IB, IC or ID, or pharmaceutically acceptable salt thereof, that is effective in treating such condition.

The present invention also relates to a pharmaceutical composition for treating a condition selected from mental retardation, developmental disorders, disruptive behavioral disorders, organic mental disorders (including dementia and psychoactive substance induced organic mental disorders), psychoactive substance abuse disorders, mood disorders, anxiety disorders, somatoform disorders, dissociative disorders, attention deficit disorder, schizophrenia and personality disorders in a human, comprising an acetylcholine, dopamine or serotonin release enhancing effective amount of a compound of the formula IA, IB, IC or ID, or a pharmaceutical acceptable salt thereof, and a pharmaceutically acceptable carrier.

The present invention also relates to a method of treating a condition selected from mental retardation, developmental disorders, disruptive behavioral disorders, organic mental disorders (including dementia and psychoactive substance induced organic mental disorders), psychoactive substance abuse disorders, mood disorders, anxiety disorders, somatoform disorders, dissociative disorders, attention deficit disorder, schizophrenia and personality disorders in a human, comprising an administering to said human an acetylcholine, dopamine or serotonin release enhancing effective amount of a compound of the formula IA, IB, IC or ID, or pharmaceutically acceptable salt thereof.

This invention also relates to a pharmaceutical composition for treating a disease or condition, the treatment or prevention of which can be effected or facilitated by enhancing acetylcholine, dopamine or serotonin release in a human, comprising an acetylcholine, dopamine or serotonin release enhancing effective amount of a compound of the formula IA, IB, IC or ID, or a pharmaceutically acceptable salt thereof, and a pharmaceutically acceptable carrier.

This invention also relates to a method of treating a disease or condition, the treatment or prevention of which can be effected or facilitated by enhancing acetylcholine, dopamine or serotonin release in a human, comprising administering to said human an acetylcholine, dopamine or serotonin release enhancing effective amount of a compound of the formula IA, IB, IC or ID, or a pharmaceutically acceptable salt thereof.

The compounds of the invention may also be used in combination with an acetylcholine esterase inhibitor to treat or prevent the foregoing conditions.

This invention also relates to a pharmaceutical composition for the treatment of Alzheimer's disease, age associated memory impairment or Parkinson's disease in a human, comprising an acetylcholine release enhancing amount of a compound of the formula IA, IB, IC or ID, or a pharmaceutically acceptable salt thereof, an acetylcholine esterase inhibiting amount of an acetylcholine esterase inhibitor or a pharmaceutically acceptable salt thereof, and a pharmaceutically acceptable carrier.

This invention also relates to a method of treating Alzheimer's disease, age associated memory impairment or Parkinson's disease in a human, comprising administering to said human an acetylcholine release enhancing amount of a compound of the formula IA, IB, IC or ID, or a pharmaceutically acceptable salt thereof, in combination with an acetylcholine esterase inhibiting amount of an acetylcholine esterase inhibitor or a pharmaceutically acceptable salt thereof.

This invention also relates to a pharmaceutical composition for the treatment of a condition selected from mental retardation, developmental disorders, disruptive behavioral disorders, organic mental disorders (including dementia and psychoactive substance induced organic mental disorders), psychoactive substance abuse disorders, mood disorders, anxiety disorders, somatoform disorders, dissociative disorders, attention deficit disorder, schizophrenia and personality disorders in a human, comprising an acetylcholine release enhancing amount of a compound of the formula IA, IB, IC or ID, or a pharmecutically acceptable salt thereof, an acetylcholine esterase inhibiting amount of an acetylcholine esterase inhibitor or a pharmaceutically acceptable salt thereof, and a pharmaceutically acceptable carrier.

This invention also relates to a method of treating a condition selected from mental retardation, developmental disorders, disruptive behavioral disorders, organic mental disorders (including dementia and psychoactive substance induced organic mental disorders), psychoactive substance abuse disorders, mood disorders, anxiety disorders, somatoform disorders, dissociative disorders, attention deficit disorder, schizophrenia and personality disorders in a human, comprising administering to said human an acetylcholine release enhancing amount of a compound of the formula IA, IB, IC or ID, or a pharmaceutically acceptable salt thereof, in combination with an acetylcholine esterase inhibiting amount of an acetylcholine esterase inhibitor or a pharmaceutically acceptable salt thereof.

DETAILED DESCRIPTION OF THE INVENTION
The preparation of compounds of the formulae IA, IB, IC, ID and 11 are described below. In the reaction schemes and discussion that follows, m, X, Z, A, $R^1$, $R^2$, $R^3$, $R^4$, $R^5$, $R^6$, $R^7$, $R^8$, $R^{11}$, $R^{12}$ $R^{13}$ and $R^{14}$ are defined as above.
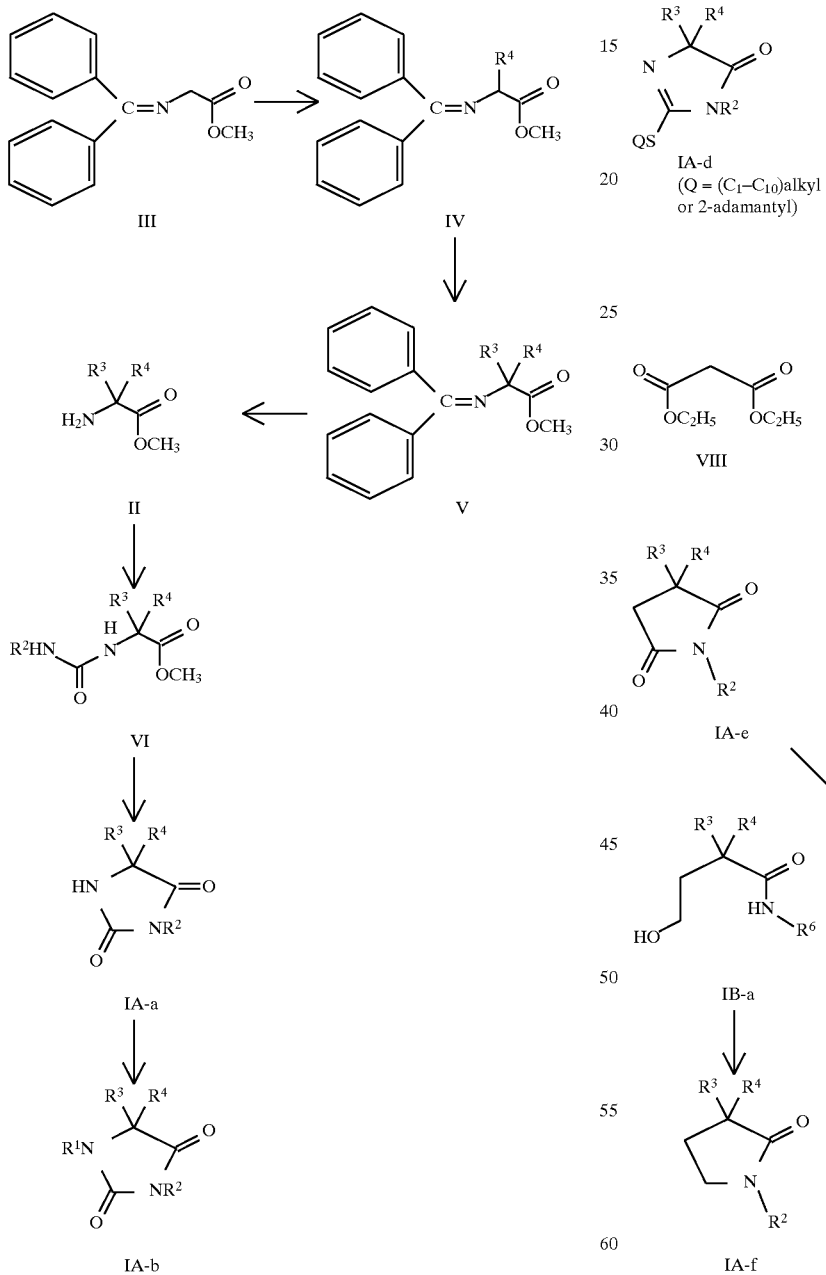
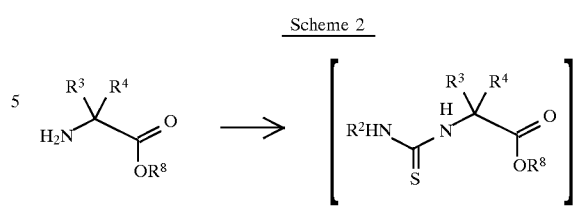

Scheme 4

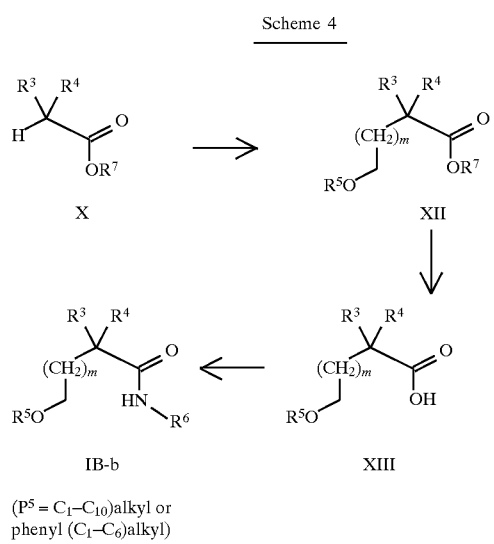

($P^5$ = $C_1$–$C_{10}$)alkyl or phenyl ($C_1$–$C_6$)alkyl)

Scheme 5

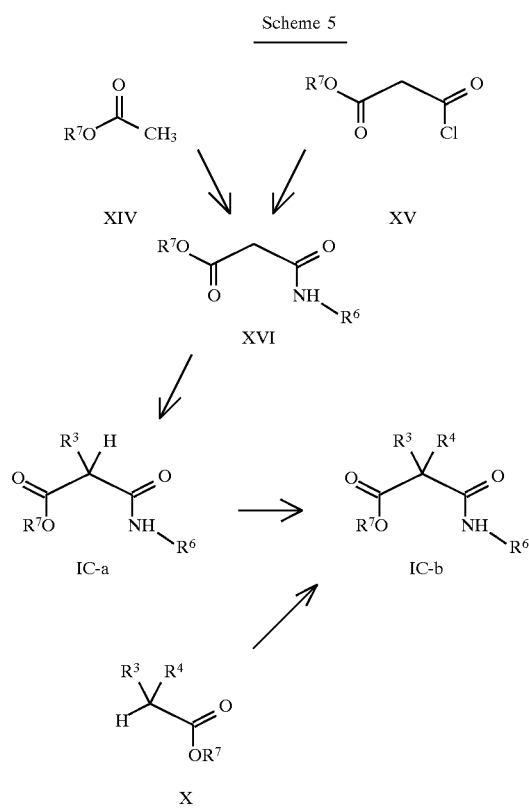

Scheme 6

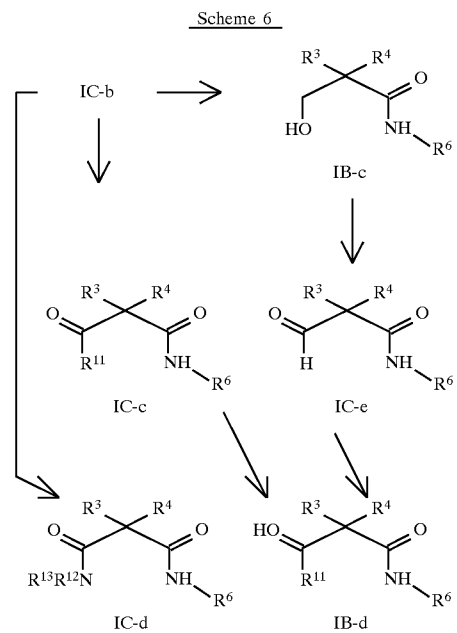

Scheme 7

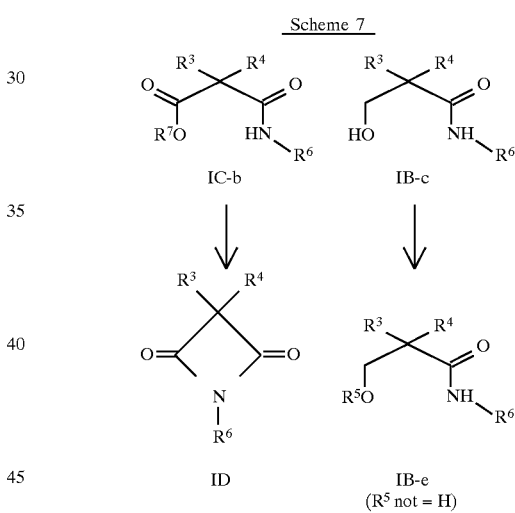

Scheme 1 illustrates a method of preparing compounds of the formula IA wherein X is $NR^1$ and Z is oxygen. Such compounds wherein $R^1$ is hydrogen are hereinafter referred to as compounds of the formula IA-a, and such compounds wherein $R^1$ is other than hydrogen are hereinafter referred to as compounds of the formula IA-b. Scheme 2 illustrates a method of preparing compounds of the formula IA wherein X is NH and Z is sulfur (hereinafter referred to as compounds of the formula IA-c) and compounds of the formula IA wherein X is N and Z is ($C_1$–$C_{10}$)alkyl—S— or 2-adamantyl—S—(hereinafter referred to as compounds of the formula IA-d).

Scheme 3 illustrates the synthesis of compounds of the formula IA wherein X is $CH_2$ and Z is oxygen (hereinafter referred to as compounds of the formula IA-e) and compounds of the formula IA wherein X is $CH_2$ and Z is (H, H) (hereinafter referred to as compounds of the formula IA-f). This scheme also illustrates the synthesis of compounds of the formula IB wherein $R^5$ and $R^{14}$ are hydrogen and m is one (hereinafter referred to as compounds of the formula IB-a). Scheme 4 illustrates the synthesis of compounds of the formula IB wherein $R^{14}$ is hydrogen and $R^5$ is ($C_1$–$C_{10}$) alkyl or phenyl-($C_1$–$C_6$)alkyl (hereinafter referred to as compounds of the formula IB-b).

Scheme 5 illustrates a method of preparing compounds of the formula IC wherein $R^4$ is hydrogen and W is $OR^7$ (hereinafter referred to as compounds of the formula IC-a) and compounds of the formula IC wherein W is $OR^7$ (hereinafter referred to as compounds of the formula IC-b).

Scheme 6 illustrates a method of synthesizing compounds of the formula IB wherein $R^5$ and $R^{14}$ are hydrogen and m is zero (hereinafter referred to as compounds of the formula IB-c), compounds of the formula IC wherein W is $R^{11}$ or hydrogen (hereinafter referred to, respectively, as compounds of the formula IC-c or IC-e). Scheme 6 also illustrates the preparation of compound of the formula IC wherein W is $NR^{12}R^{13}$ (hereinafter referred to as compounds of the formula IC-d) and compounds of the formula IB wherein R5 is hydrogen, m is zero and $R^{14}$ is $R^{11}$ (e selected from ($C_1$–$C_6$) alkyl) (hereinafter referred to as compounds of the formula IB-d).

Scheme 7 depicts a method of preparing compounds of the formula ID and compounds of the formula IB wherein m is zero, $R^{14}$ is hydrogen and $R^5$ is other than hydrogen (hereinafter referred to as compounds of the formula IB-e).

Referring to scheme 1, a compound of the formula III is reacted with potassium bis(trimethylsilyl)amide in THF (tetrahydrofuran) at a temperature of about −70° C. After stirring for about 30 minutes, a compound of the formula 2-, 3- or 4pyridinylmethyl-X, wherein X is an appropriate leaving group (e, chloride or bromide), is added and the reaction mixture is allowed to warm to about ambient temperature. This reaction yields a compound of the formula IV wherein $R^4$ is 2-, 3- or 4-pyridinylmethyl, which can be isolated or reacted in situ to form a compound of the formula V.

Addition of the $R^3$ substituent to the compound of formula IV yields a compound of the formula V. This is accomplished by carrying out the same procedure described above for making the compound of formula IV, with the exception that a compound of the formula $R^3X$ is used instead of 2-, 3- or 4-pyridinylmethyl-X. ($R^3X$ may, however, as indicated above, be 2, 3-or 4-pyridinylmethyl-X.)

Compounds of the formula II may be formed by reacting the corresponding compounds of the formula V with an acid. The acid is preferably a mineral acid such as hydrochloric, nitric or sulfuric acid. This reaction is typically carried out using an organic cosolvent such as ethyl ether, tetrahydrofuran (THF) or acetonitrile, preferably ethyl ether. The reaction temperature may range from about −5° C. to about 35° C., and is preferably between about 0° C. and about room temperature.

Reaction of the resulting compound of formula II with an isocyanate of the formula $R^2NCO$ yields the corresponding urea of formula VI. Generally, this reaction is carried out in a protic solvent such as methanol, ethanol or methylene chloride, with methanol and ethanol being preferred, at a temperature from about room temperature to about 78° C., preferably at about the reflux temperature of the solvent. The reaction is preferably carried out for about six to eight hours, but can be carried out for longer or shorter periods (e.g., from about a half day to about two days).

The urea of formula VI can be isolated or converted in situ to the corresponding hydantoin derivative of formula IA-a. (Thin layer chromatography (TLC) can be used to determine when the starting material from the preceding reaction has been consumed.) The conversion is effected by heating the compound of formula VI in the presence of a catalytic amount of potassium cyanide in a reaction inert solvent that is the same or similar to that used in the preceding reaction. This reaction is preferably conducted at the reflux temperature of the solvent, though lower temperatures (e.g., about ambient temperature to about 78° C.) are also suitable.

Compounds of the formula IA-b may be formed by reacting the corresponding compounds of the formula IA-a with a strong base (e.g., sodium hydride, lithium diisopropylamide, lithium hydride or potassium hydride), followed by a compound of the formula $R^1X$, wherein X is a leaving group (e.g., chloride, iodide or bromide), and the preferred base is sodium hydride and the preferred leaving group is iodide or bromide. The solvent is typically an aprotic solvent such as THF, dimethylformamide (DMF) or an ether such as ethyl ether. It is preferably DMF. The reaction temperature can range from about −78° C. to about 70° C. A temperature of about 0° C. to about room temperature is preferred.

Referring to scheme 2, compounds of the formula IA-c and IA-d may be formed as follows. A compound of the formula 11 is reacted with a compound of the formula $R^2NCS$ to form the corresponding compound of formula IA-c. This reaction, which proceeds through an intermediate of the formula VII, is generally carried out using similar solvents and under similar conditions as those described above for the formation of the urea of formula VI. When $R^2$ is adamantyl, it is preferable to use a large excess of the reactant $R^2NCS$ and to let the reaction proceed for a period of about two days to one week.

The resulting compound of formula IA-c can then be converted into the corresponding compound of formula IA-d by reacting it with a compound of the formula QX wherein Q is ($C_1$–$C_6$)alkyl, 2-adamantyl, phenyl—C(=O)$CH_2$- or ($C_1$–$C_6$)alkyl—O—C(=O)—$CH_2$— and X is a leaving group, as defined above. This reaction is typically carried out in a polar solvent such as THF, DMF or acetonitrile or acetone, preferably acetone, in the presence of a base scavenger such as a carbonate or an organic tertiary amine. Potassium carbonate is preferred. The reaction temperature can range from about −78° C. to about 140° C., with about 0° C. to about room temperature being preferred. When Q is adamantyl or another bulky substituent such as cyclohexyl, the reaction is preferably carried out in DMF at a temperature from about 25° C. to about the reflux temperature.

Referring to scheme 3, compounds of the formula IX may be prepared by reacting diethylmalonate with sodium ethoxide, followed by 2-, 3- or 4-pyridinylmethyl-X, wherein X is a leaving group (e.g., chloro or bromo). The monoalkylated product is then reacted with sodium ethoxide, followed by a compound of the formula $R^3X$, wherein X is a leaving group, as defined above. (The reactions with 2-, 3- or 4-pyridylmethyl-X and $R^3X$ can be carried out simultaneously or sequentially. However, hen $R^3$ and $R^4$ are different, it is preferable to isolate and purify the monoalkylated product prior to formation of the dialkylated product with $R^3X$.) The bisester is then hydrolyzed with two to three equivalents of sodium or potassium hydroxide. Preferably, after addition of the sodium or potassium hydroxide, the reaction mixture is stirred for up to about 48 hours. These ester hydrolyses reactions are generally conducted at a temperature of about 0° C. to about 60° C. in an ether/alcohol/water solvent, preferably a THF:methanol:water mixture.

The compound of formula IX can be converted into the corresponding compound of the formula X by reacting it at a temperature of about 0° C. to about 50° C. with an excess of an anhydrous acid such as hydrochloric or hydrobromic acid, in the amount of one equivalent of acid per basic functionality in the compound of formula IX (eg., four equivalents of acid if both $R^3$ and $R^3$ are 4-pyridinylmethyl), and with an alcohol of the formula $R^7OH$, and then evaporating the reaction mixture to dryness.

Alternatively, when $R^3$ and $R^4$ are acid sensitive, compounds of the formula X can be prepared as described by Krapcho et al., *J. Org. Chem.*, 43, 138 (1978). This procedure involves treatment of the bis-alkylated malonate with dimethylsulfoxide (DMSO), lithium chloride and water, and is exemplified in Example 12 below.

The pyrrolidine-2,5-dione derivative of formula IA-e may be prepared by reacting the corresponding compound of formula X with an amide base followed by a compound of the formula $R^2NHCOCH_2X$, wherein X is a leaving group, as defined above. Appropriate bases include lithium diisopropylamide, lithium hexamethyldisilazide and lithium diethylamide. Suitable solvents include aprotic solvents such as THF, ethyl ether, DMF, benzene and toluene. The reaction may be conducted at temperatures ranging from about −78° C. to about room temperature. Preferably, this reaction is carried out in THF, using lithium diisopropylamide as the base and bromide as the leaving group, at a temperature from about −78° C. to about room temperature.

Reaction of the resulting compound of the formula IA-e with a borohydride yields the corresponding compounds of the formulae IB-a and XI. The major product formed is the compound of formula IB-a. This reaction is generally carried out in a protic solvent such as a lower alcohol, preferably isopropanol, at a temperature from about −20° C. to about 50° C., preferably at about room temperature, using a large excess of borohydride. Sodium borohydride is the preferred reactant, though other borohydrides (e., lithium borohydride) may also be used.

The compounds of formula IB-a formed in the above step can be converted into the corresponding compounds of the formula IA-f by reacting them with a phosphine (e.g., tributylphosphine or triphenylphosphine) and an azodicarboxylate (e.g., diisopropylazodicarboxylate or diethylazodicarboxylate). Suitable solvents for this reaction (a Mitsunobu reaction) include aprotic solvents such as THF, methylene chloride or acetonitrile, with THF being preferred. Suitable temperatures range from about 0° C. to about 40° C., with about room temperature being preferred.

Compounds of the formula IB-b may be prepared as described below and depicted in scheme 4. Referring to scheme 4, a compound of the formula X is reacted with lithium diisopropylamide in THF at a temperature from about −78° C. to about 0° C. A compound of the formula $R^5OCH_2(CH_2)_mBr$, wherein $R^5$ is $(C_1-C_{10})$alkyl or phenyl-$(C_1-C_6)$ alkyl, is then added and the reaction mixture is allowed to warm to about 0° C.

The above reaction produces a compound of formula XII, which is then hydrolyzed to form the corresponding compound of formula XIII. The hydrolysis may be accomplished using standard procedures well known to those skilled in the art. It is preferably accomplished by reacting the compound of formula XII with sodium hydroxide in a solvent such as methanol/water, ethanol/water or THF/water, at a temperature from about room temperature to about 70° C., preferably at about 70° C.

The corresponding compound of formula IB-b (L, wherein $R^5$ is $(C_1-C_6)$alkyl or phenyl-$(C_1-C_6)$alkyl) is then prepared by reacting the compound of formula XIII formed in the above step with a compound of the formula $R^6NH_2$ and 1-(3-dimethylaminopropyl)-3-ethylcarbodiimide hydrochloride. Typically, this reaction is conducted in a polar solvent such as THF or a THF/water mixture, preferably in a THF/water mixture, at a pH of about 5–7 and a temperature of about 0° C. to about 60° C., preferably at about room temperature.

Compounds of the formula IB wherein $R^5$ is $(C_1-C_6)$ alkyl—C(=O)— may be prepared by reacting the corresponding compounds wherein $R^5$ is $(C_1-C_6)$alkyl or phenyl $(C_1-C_6)$alkyl with an anhydride of the formula $R^9$—C(=O)—O—C(=O)—$R^{10}$, wherein $R^9$ and $R^{10}$ are independently selected from $(C_1-C_6)$alkyl, in the presence of a catalytic amount of 4-dimethylaminopyridine. Appropriate solvents include aprotic solvents such as pyridine, pyridine/THF or methylene chloride. The reaction may be conducted at temperatures ranging from about 0° C. to about 60° C. It is preferably conducted in pyridine at a temperature from about 0° C. to about room temperature.

Scheme 5 illustrates two methods of preparing compounds of the formula IC wherein W is $OR^7$. Referring to scheme 5, the first method involves reacting a compound of the formula XIV with a compound of the formula $R^6$—N=C=O in the presence of lithium diisopropylamide (LDA) to form a compound of the formula XVI. This reaction is typically carried out in an ether, dioxane or THF solvent at a temperature of about −78° C. to about 0° C. It is preferably carried out in THF at about −78° C.

Alternatively, intermediates of the formula XVI can be prepared by reacting a compound of the formula XV with a compound of the formula $NH_2R^6$ in the presence of a base. This reaction, which is a Schotten-Baumann reaction, is preferably conducted using potassium hydroxide as the base and ethyl ether as the solvent, or using triethylamine as the base and methylene chloride as the solvent. The reaction may be carried out at temperatures ranging from about −20° C. to about 40° C., and is preferably carried out from about 0° C. to about room temperature.

Compounds of the formula XVI so formed can be converted into active compounds of the formula IC wherein $R^4$ is hydrogen and W is $OR^7$ (i.e., compounds of the formula IC-a) via a malonic ester alkylation. The malonic ester alkylation is accomplished by reacting the compound of formula XVI with a compound of the formula $XCH_2Het$, wherein X is chlorine or bromine, in the presence of a sodium alkoxide of the formula $NaOR^7$ and an alcohol solvent of the formula $R^7OH$ at a temperature from about 0° C. to about 60° C. Preferably, this reaction is carried out at about room temperature.

A second malonic ester alkylation may be used to add a non-hydrogen $R^4$ group to the compound of formula IC-a formed in the above step, converting it into the analagous compound of the formula IC-b, as depicted in scheme 5. This reaction is carried out under the same conditions and using the same reagents described above.

An alternate method of preparing compounds of the formula IC-b is to react a compound of the formula X, as depicted in scheme 5, with a compound of the formula $R^6N=C=O$ in the presence of lithium diisopropylamide, using solvents and conditions similar to those described above for the preparation of the compounds of the formula XVI from the compounds of the formula XIV.

Scheme 6 illustrates the preparation of compounds of the formulae IB-c, IB-d, IC-c, IC-d and IC-e from compounds of the formula IC-b. Referring to scheme 6, reduction of a compound of the formula IC-b yields the corresponding compound of formula IB-c ($R^5$ is hydrogen and m is zero). The reduction can be accomplished using sodium borohydride or lithium borohydride as the reducing agent, and using methanol, ethanol, or isopropanol, preferably methanol, as the solvent. Suitable reaction temperatures range from about 0° C. to about room temperature. About room temperature is preferred.

Compounds of the formula IB-c can be converted into the corresponding compounds of the formula IC-e by the following two-step procedure. First, the compound of formula IB-c is reacted with oxalyl chloride [$(ClCO)_2$] in dimethylsulfoxide (DMSO) and either methylene chloride, chloroform or diethylether, preferably methylene chloride, at a temperature from about −78° C. to about −55° C., preferably at about −78° C. Then, triethylamine is added and the reaction mixture is allowed to warm to room temperature.

Subjecting a compound of the formula IC-e from the above step to a Grignard reaction produces the corresponding compound of the formula IB-d. This reaction is generally conducted using a Grignard reagent of the formula $R^{11}MgX$, wherein X is chlorine or bromine, in a THF or ethyl ether solvent, preferably in THF, and in the presence of cuprous bromide. Preferably, the reaction is begun at about −78° C. and allowed to warm to about room temperature.

Compounds of the formula IC-d can be prepared by reacting the corresponding compounds of the formula IC-b with a compound of the formula $LiNR^{12}R^{13}$. This reaction is generally carried out in a THF or ethyl ether solvent, preferably in THF, at a temperature about −78° C. to about room temperature, preferably from about 0° C. to about room temperature.

Compounds of the formula IC-b, the starting material for the reactions of scheme 6, may also be used to prepare the corresponding compounds of the formula IC-c and compounds of the formula IB-d by the following procedure. The compound of formula IC-b is first treated with a Grignard reagent of the formula $R^{11}MgX$, wherein X is chlorine or bromine, in the presence of cuprous bromide in an ethyl ether solvent at a temperature from about 0° C. to about room temperature, preferably at about room temperature. The resulting compound of the formula IC-c is then reduced with either sodium borohydride or lithium brohydride to produce the corresponding compound of formula IB-d. Typically, the latter reaction is carried out in a lower alkanol solvent such as methanol, ethanol or isopropanol, preferably methanol, at a temperature from about 0 ° C. to about room temperature, preferably at about room temperature.

Scheme 7 illustrates the preparation compounds of the formula ID from compounds of the formula IC-b. It also illustrates the preparation of compounds of the formula IB-e from compounds of the formula IB-c.

To form a compound of the formula ID, a corresponding compound of the formula IC-b is subjected to a Grignard reaction. The Grignard reagent is preferably compound of the formula $CH_3MgBr$ and the reaction is preferably carried out in THF in the presence of cuprous bromide. Suitable reaction temperatures may range from about 0° C. to about 50° C., with about 50° C. being preferred.

Compounds of the formula IB-e may be prepared by reacting the corresponding compound of the formula IB-c with a strong base and an alkyl halide of the formula $R^5X$ wherein X is a halogen, at a temperature from about 0° C. to about 50° C. This reaction, which is known as Williamson ether synthesis, is preferably carried out at about room temperature using sodium hydride as the base.

The preparation of other compounds of the formulae IA, IB, IC and ID not specifically described in the foregoing experimental section can be accomplished using combinations of the reactions described above that will be apparent to those skilled in the art.

In each of the reactions discussed or illustrated in schemes 1 to 7 above, pressure is not critical unless otherwise indicated. Pressures from about 0.5 atmospheres to about 4 atmospheres are generally acceptable, and ambient pressure, i.e., about 1 atmosphere, is preferred as a matter of convenience.

The novel compounds of the formulae IA, IB, IC and ID and the pharmaceutically acceptable salts thereof (hereinafter "the therapeutic compounds of this invention") are useful as neurotransmitter release enhancers, i.e., they possess the ability to enhance or stimulate the release of neurotransmitters such as acetylcholine, dopamine and serotonin in humans. They are therefore able to function as therapeutic agents in the treatment of a variety of conditions in humans, the treatment or prevention of which can be effected or facilitated by the enhancement or stimulation of acetylcholine, dopamine or serotonin release. Such conditions include Alzheimer's disease, age associated memory impairment and Parkinson's disease. They also include mental retardation, developmental disorders, disruptive behavioral disorders, organic mental disorders (including dementia and psychoactive substance induced organic mental disorders), psychoactive substance abuse disorders, mood disorders, anxiety disorders, somatoform disorders, dissociative disorders, attention deficit disorder, schizophrenia and personality disorders.

The compounds of the formulae IA, IB, IC and ID that are basic in nature are capable of forming a wide variety of different salts with various inorganic and organic acids. Although such salts must be pharmaceutically acceptable for administration to animals, it is often desirable in practice to initially isolate a compound of the Formula I from the reaction mixture as a pharmaceutically unacceptable salt and then simply convert the latter back to the free base compound by treatment with an alkaline reagent and subsequently convert the latter free base to a pharmaceutically acceptable acid addition salt. The acid addition salts of the base compounds of this invention are readily prepared by treating the base compound with a substantially equivalent amount of the chosen mineral or organic acid in an aqueous solvent medium or in a suitable organic solvent, such as methanol or ethanol. Upon careful evaporation of the solvent, the desired solid salt is readily obtained. The desired acid salt can also be precipitated from a solution of the free base in an organic solvent by adding to the solution an appropriate mineral or organic acid.

The therapeutic compounds of this invention can be administered orally, transdermally (e.g., through the use of a patch), parenterally or topically. Oral administration is preferred. In general, these compounds are most desirably administered in dosages ranging from about 1.0 mg up to about 500 mg per day, preferably from about 1 to about 100 mg per day, although variations may occur depending on the weight and condition of the person being treated and the particular route of administration chosen. In some instances, dosage levels below the lower limit of the aforesaid range may be more than adequate, while in other cases still larger doses may be employed without causing any harmful side effect, provided that such larger doses are first divided into several small doses for administration throughout the day.

The therapeutic compounds of the invention may be administered alone or in combination with pharmaceutically acceptable carriers or diluents by either of the two routes previously indicated, and such administration may be carried out in single or multiple doses. More particularly, the novel therapeutic compounds of this invention can be administered in a wide variety of different dosage forms, i.e., they may be combined with various pharmaceutically acceptable inert carriers in the form of tablets, capsules, lozenges, troches, hard candies, powders, sprays, creams, salves, suppositories, jellies, gels, pastes, lotions, ointments, elixirs, syrups, and the like. Such carriers include solid diluents or fillers, sterile aqueous media and various non-toxic organic solvents, etc. Moreover, oral pharmaceutical compositions can be suitably sweetened and/or flavored.

For oral administration, tablets containing various excipients such as microcrystalline cellulose, sodium citrate, calcium carbonate, dicalcium phosphate and glycine may be employed along with various disintegrants such as starch (and preferably corn, potato or tapioca starch), alginic acid and certain complex silicates, together with granulation binders like polyvinylpyrrolidone, sucrose, gelatin and acacia. Additionally, lubricating agents such as magnesium stearate, sodium lauryl sulfate and talc are often very useful for tabletting purposes. Solid compositions of a similar type may also be employed as fillers in gelatin capsules; preferred materials in this connection also include lactose or milk sugar as well as high molecular weight polyethylene glycols. When aqueous suspensions and/or elixirs are desired for oral administration, the active ingredient may be combined with various sweetening or flavoring agents, coloring matter or dyes, and, if so desired, emulsifying and/or suspending agents as well, together with such diluents as water, ethanol, propylene glycol, glycerin and various like combinations thereof.

For parenteral administration, solutions of a compound of the present invention in either sesame or peanut oil or in aqueous propylene glycol may be employed. The aqueous solutions should be suitably buffered if necessary and the liquid diluent first rendered isotonic. These aqueous solutions are suitable for intravenous injection purposes. The oily solutions are suitable for intra-articular, intra-muscular and subcutaneous injection purposes. The preparation of all these solutions under sterile conditions is readily accomplished by standard pharmaceutical techniques well-known to those skilled in the art.

Additionally, it is also possible to administer the compounds of the present invention topically and this may preferably be done by way of creams, jellies, gels, pastes, ointments and the like, in accordance with standard pharmaceutical practice.

The activity of the compounds of the present invention as acetylcholine or other neurotransmitter release enhancers may be determined by their ability, relative to a control, to enhance in vitro the potassium stimulated release of acetylcholine or another neurotransmitter in rat brain tissue. This procedure is described below.

In Vitro Potassium Stimulated Neurotransmitter Release

Male, Sprague Dawley rats (180–250 g) are decapitated and their brains removed and cooled by immersion in a cold, oxygenated Krebs buffer containing 124 mM sodium chloride, 10 mM glucose, 5 mM potassium chloride, 26 mM sodium bicarbonate, 1.2 mM potassium dihydrogen phosphate, 1.3 mM magnesium sulfate and 0.75 mM calcium chloride. The brains are placed on a cold plate and the striatal tissue is removed and chopped with a tissue chopper (e.g., a McIlwain tissue chopper) to produce 0.4×0.4 mm blocks of tissue. The tissue is washed 4 times with the oxygenated buffer and incubated for 30 minutes in a buffer containing either ($^3$H)choline, ($^3$H)dopamine or ($^{14}$C) serotonin. In assays using dopamine or serotonin, 10 µM of pargyline are added. The preparation is washed 8 times to remove any unincorporated label and then loaded into 5 ml syringes with their cut end sealed with a Nitex nylon screen. The syringes are repeatedly incubated for 4 minutes in the oxygenated buffer. Potassium depolarization with 15 mM potassium chloride (tonicity maintained by a reduction in the concentration of sodium chloride) is introduced at the 7th (S1) and the 15th (S2) four minute fractions. The drugs are introduced three fractions (12 min) before the second (S2) potassium stimulation and remain in the bath throughout S2. At the end of the experiment, the tissue is solubilized in 1% SDS sodium dodecyl sulfate and the amount of label left in the tissue is determined by liquid scintillation counting. The release of the label is expressed as a fractional release by dividing the CPMs (counts per minute) released into the 4 minute incubation buffer with the CPMs calculated to be present in the tissue at the time of each four minute fraction. To determine drug effects on release, the S2/S1 of drug treated conditions are compared to the S2/S1 of control slices and expressed as a percent of control. In this way, each slice condition serves as its own control.

When tested according to the above procedure, all compounds exemplified in this application exhibited at least a 10 percent increase in acetylcholine release stimulation relative to the control.

The potentiating effect of acetocholine choline release enhancers DP-996, CP-312,301 and CP-241,108, which are depicted below, on hypothermia in rats induced by the acetylcholinesterase inhibitor THA (tetrahydroaminoacridine) is demonstrated by the data in Table I below.

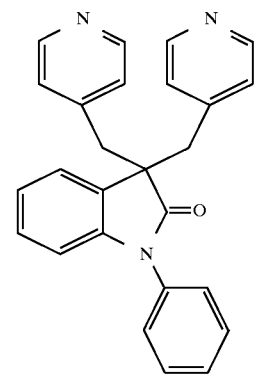

DuP-996

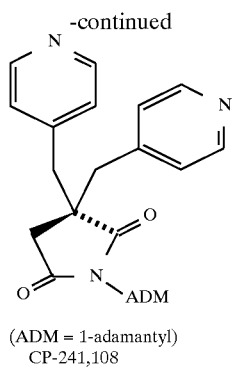

(ADM = 1-adamantyl)
CP-241,108

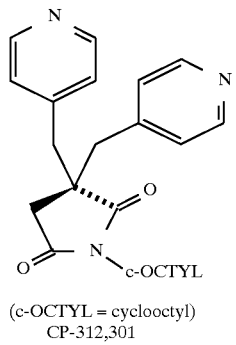

(c-OCTYL = cyclooctyl)
CP-312,301

The data in Table I was generated according to the following protocol.

Method. Male CD rats housed under standard laboratory conditions, weighing from 250–400 grams serve as subjects in these experiments. Compounds are dissolved in distilled water and are administered subcutaneously. Injection volume is typically 1 ml/kg. Animals are randomly assigned to treatment groups and are individually placed into plastic cages for a 30 minute habituation period. Test compounds are administered 30 minutes prior to the cholinesterase inhibitor, THA, which is administered at a doses of 3.2 mg/kg. A digital thermometer with a small probe is used for measurement of rectal temperatures at baseline (T-60) and at 30, 60, and 120 minutes after administration of THA. Data are analyzed with ANOVA followed by Newman-Keuls multiple comparisons.

TABLE I

| | Change from Baseline (°C.) | | |
|---|---|---|---|
| | 30 min. | 60 min. | 120 min. |
| Experiment 1 | | | |
| Vehicle + Vehicle | +0.14 | +0.12 | −6.28 |
| Vehicle + THA/3.2 | +0.06 | −0.17 | −1.02 |
| Dup-996/1.0 + THA | +0.0 | −0.25 | −1.14 |
| Dup-996/3.2 + THA | −0.10 | −0.37 | −1.13 |
| Dup-996/10 + THA | −0.96** | −1.13** | −1.63 |
| Experiment 2 | | | |
| Vehicle + Vehicle | +1.18 | +0.88 | +0.02 |
| Vehicle + THA/3.2 | +0.46 | −0.20 | −1.52 |
| CP312,301/3.2 + THA | −0.10 | −0.54 | −1.22 |
| CP312,301/10 + THA | −0.48** | −1.44** | −2.02 |
| Experiment 3 | | | |
| Vehicle + Vehicle | −0.18 | +0.05 | −0.85 |
| Vehicle + THA/3.2 | −0.28 | −0.40 | −2.15 |
| CP241,108/.032 + THA | −0.27 | −0.55 | −1.67 |

TABLE I-continued

| | Change from Baseline (°C.) | | |
|---|---|---|---|
| | 30 min. | 60 min. | 120 min. |
| CP241,108/0.32 + THA | +0.30 | 0 | −1.25 |
| CP241,108/3.2 + THA | −0.48 | −1.28* | −1.1 |

*, ** = p < 0.05, 0.01 different from the Vehicle + THA/3.2 group = potentiation The present invention is illustrated by the following examples. It will be understood, however, that the invention is not limited to the specific details of these examples.

EXAMPLE 1

3-Phenyl-5-pyridinyl-4ylmethyl-imidazolidine-2,4-dione

A. 2-Benzhydrylideneamino-3-pyridin-4-yl-propionic acid methyl ester

Potassium bis(trimethylsilyl)amide (0.344 g, 1.72 mmol) was added under nitrogen atmosphere to 10 ml of dry THF and the resultant solution was cooled to −70° C. To this clear solution was added 0.436 g (1.72 mmol) of methyl benzhydrylideneamino acetate and the resulting yellowish red solution was allowed to stir at −70° C. for 30 min. at which point 0.219 g (1.72 mmol) of 4-picolyl chloride was added. The reaction was allowed to warm to ambient temperature and stirring was continued for two hours. At this point, the monoalkylated product could be isolated by quenching the reaction in equal volumes of ethyl acetate/water, separating the organic layer, drying over sodium sulfate ($NaSO_4$), concentrating in vacuo and chromatographing on silica gel to yield the desired product as a crystalline solid.

$^1$H NMR ($CDCl_3$): 3.12–3.48 (m-2H), 3.73 (s-3H), 4.26–4.30 (m-i H), 6.67 (d-2H), 6.95 (d-2H), 7.25–7.39 (m-6H), 7.54 (d-2H), 8.39 (d-2H). $^{13}$C NMR ($CDCl_3$): 39.12, 52.54, 66.21, 125.24, 127.7, 128.23, 128.48, 128.78, 128.91, 130.7, 135.79, 139.1, 147.19, 149.68, 171.63, 171.81.

B. 2-Benzhydrylideneamino-3pyridin yl-2:pyridin4ylmethyl-propionic acid methyl ester The reaction was cooled back down again to −70° C., an additional 0.344 g (1.72 mmol) of potassium bis(trimethylsilyl)amide was added and the reaction was stirred for an additional 30 min. at −70° C. After a clear solution was obtained, an additional 0.219 g (1.72 mmol) of 4-picolyl chloride was added. The reaction was then allowed to warm to ambient temperature, stirred for an additional 18 hours, and quenched in equal volumes of ethyl acetate/water (EtOAc/$H_2O$). The organic layer was separated, washed with water (1X), brine (1X), dried over $NaSO_4$, filtered and concentrated. The crude product was chromatographed on silica gel starting out with 100% ethyl acetate (EtOAc) to yield 0.13 g (22%) of the monoalkylated product. The column eluent was then switched to 4:1 ethyl acetate/methanol (EtOAc/MeOH) to afford 0.527 g (70.5%) of the title compound as a yellow foam, which was crystallized from ethyl acetate/hexane (EtOAc/Hex).

$^1$H NMR ($CDCl_3$): 3.11 (s-3H), 3.25 (s-4H), 6.79 (d-2H), 7.11 (d-4H), 7.27–7.44 (m-6H), 7.55 (d-2H), 8.5 (d4H). 13C NMR ($CDCl_3$): 44.05, 51.11, 69.69, 125.87, 127.72, 127.84, 128.02, 128.44, 128.59, 130.42, 136.14, 140.27, 145.61, 149.32, 167.16, 172.73.

The title compounds of "A" and "B" above were also prepared by a method that employed a modification of the above procedures in that for the second addition, only ½ equivalent of the potassium bis(trimethylsilyl)amide and 4-picolyl chloride reagents were added. Thus, under a nitrogen ($N_2$) atmosphere, 80 ml of dry THF and 3.96 g (19.9 mmol) were combined, stirred into solution and cooled to −70° C. Methyl 30 benzhydrylideneamino acetate (5.02 g, 19.9 mmol) was added in one portion, stirred into solution and the temperature was maintained for 30 min. at −70° C., at which time 2.53 g (19.9 mmol) of 4-picolyl chloride was added. The reaction was allowed to warm to ambient temperature, stirred for 2 hours and then cooled back down to −70° C. Additional (2.0 g,10 mmol) was added and the reaction was stirred until all solids were dissolved. After an additional 30 min. at −700° C., an additional 1.25 g (9.8 mmol) of 4-picolyl chloride was added and the reaction was allowed to warm to room temperature and stirred for an additional 18 hours. Workup was carried out as described above to yield 3.17 g of the monoalkylated product (46% yield) and 3.12 g of the bisalkylated product (47.9% yield).

C. 2-Amino-3-pyridin-4yl-2-pyridin-4-ylmethyl-propionic acid methyl ester (Tris HCl salt)

In a single neck round bottom flask were combined diethyl ether (10 ml) and bispyridylmethyl glycine imine (0.51 g, 1.17 mmol). The resulting suspension was cooled to 0° C., 1N hydrochloric acid (HCl) (3.4 ml) was added and reaction was allowed to stir at 0° C. until all material was dissolved, at which point it was allowed to warm to room temperature and stirred for an additional 18 hours. The ether layer was separated, and then the aqueous portion was reextracted with ether (1X) and concentrated in vacuo to give the crude title compound Methanol was added and the resultant solution was concentrated in vacuo (2X) to give the title compound, which was triturated with ether to yield 0.4 g (88.9%) of such compound as a pale yellow solid.

The free base of the above title compound was prepared as follows:

Bispyridylmethyl glycine imine tri HCl salt (12.3 g, 28.3 mmol) was suspended in diethyl ether ($Et_2O$) (225 ml) and cooled to 0° C. 1N HCl (89 ml) was added dropwise and the solution was allowed to stir at 0° C. until all solids were in solution and then allowed to stir at room temperature over night. The $Et_2O$ layer was separated and the aqueous extract was washed with additional $Et_2O$ (1×200 ml). The pH of the aqueous portion was adjusted to greater than 8 with solid sodium bicarbonate ($NaHCO_3$) and this solution was saturated with sodium chloride (NaCl) and extracted with $CH_2Cl_2$ (2×150 ml). Extracts were combined, dried over $NaSO_4$ and concentrated in vacuo to yield 7.12 g (93.7%) of free base as a solid.

$^1$H NMR ($CDCl_3$): 1.57 (broad singlet-2H), 2.77 (d-2H), 3.24 (d-2H), 3.61 (s-3H), 7.04 (d-4H), 8.46 (d4H). $^{13}$C NMR ($CDCl_3$): 45.56, 52.17, 62.56, 125.12, 144.65, 149.86, 175.06.

Prepared in similiar fashion were the 2-amino-3-pyridin-4yl-propionic acid methyl ester bis HCl salt and the corresponding free base.

Bis HCl salt: $^1$ H NMR ($D_2O$): 3.52–3.7 (m-2H), 3.79(s-3H), 4.67–4.69(m-1 H), 8.06 (d-2H), 8.77 (d-2H). $^{13}$C NMR ($D_2O$): 38.09, 54.89, 56.43, 130.81, 143.87, 159.17, 171.48.

EXAMPLE 2

3-(Benzyl)-5-pyridin-4-ylmethyl-imidazolidine-2.4-dione

A. 2-(3-(1 -Benzyl-ureido)-3-pyridin-4-yl-propionic acid

Under a nitrogen ($N_2$) atmosphere were combined 10 mls of methylene chloride ($CH_2Cl_2$), 0.18 g (1 mmol) of monopyridylmethyl methylglycinate and 0.133 g (1 mmol) of benzylisocyanate. The reaction was allowed to stir at room temperature for 18 hours. TLC indicated all starting material was consumed. The crude reaction mixture was concentrated and the title compound was crystallized from EtOAc/Hex (ethyl acetate/hexane).

B. 3-(Benzyl)-5-pyridin-4-ylmethyl-imidazolidine-2.4-dione

The resulting urea from step A was combined with 10 ml of EtOH and 5–10 mg of potassium cyanide (KCN) and heated under reflux until cyclization was complete (reaction progress was monitored by TLC). After 2 hours, the reaction was allowed to cool, was concentrated and was partitioned between 35 ml EtOAc/5ml $H_2O$. The organic layer was separated, dried and concentrated to afford the title compound, which was crystallized from EtOAc/$Et_2O$ to yield 0.13 g of the title compound.

EXAMPLE 3

3-(1 -Adamantyl)-5.5-bis-pyridin-4ylmethyl-imidazolidine-2.4-dione

A. 2-(3-(1 -adamantyl-ureido))-3-pyridin-4-yl-2-pyridin-4-yl methyl-propionic acid Under a nitrogen ($N_2$) atmosphere were combined 0.354 g (2 mmol) of 1-adamantylisocyanate, 0.271 g (1 mmol) of bispyridylmethyl methyl glycinate and 15 ml of ethanol (EtOH) and the resulting solution was allowed to reflux until the reaction was complete as determined by thin layer chromatography (TLC), (6–8 hours). The reaction mixture was then cooled, concentrated in vacuo, and the product was crystallized from isopropylether to yield 0.34 g (81.7%) of the title compound.

B. 3-(1 -Adamantyl)-5,5-bis-pyridin-4ylmethyl-imidazolidine-2,4-dione

The resulting urea from 0.29 g (0.65 mmol) was then combined with 15 ml of EtOH, 5–10 mg of KCN and the resultant solution was allowed to reflux until cyclization was complete (approx. two hours; the progress of the cyclization was monitored by thin layer chromatography). The reaction mixture was allowed to cool, was concentrated in vacuo and crude product was dissolved in 50 ml of EtOAc/5 ml MeOH. The organic solution was washed with $H_2O$ (1×5 ml), brine (1X), was dried over $Na_2SO_4$, was filtered and concentrated in vacuo to afford crude product which was isolated by filtration after trituration with EtOAc/Hex to yield 0.23 g (85.2%) of the title compound as a white solid, m.p. 284.5°–286° C.

When isolation of urea was deemed not desirable, coversion of the methylglycinate to the hydantoin was carried out in one step providing all of the amino acid ester was consumed before KCN was added.

C. 3-(1-Adamantyl)-5.5-bis-pyridin-4ylmethyl-imidazolidine-2,4-dione bis HCl salt To a rapidly stirring suspension of 1.91 g, (46 mmol) of the above hydantoin from step E in 50 ml of EtOAc was added in one portion 20 ml of EtOAc saturated with hydrogen chloride (HCl) gas. The suspension was allowed to stir for 15 min., an equal volume of $Et_2O$ was added, stirring was continued for 10 min., and then the white solids were filtered using a sintered glass funnel. The solids were washed well with $Et_2O$ and dried under $N_2$ to yield 2.31 g of the title compound.

¹H NMR (D₂0): 1.48–1.60 (m-6H), 1.73 (d-6H), 1.93 (bs-3H), 3.5 (d-2H), 3.67 (d-2H), 7.91 (d4H), 8.78 (d-4H).
¹³C NMR (D₂0): 31.98, 32.09, 37.94, 38.04, 41.76, 41.90, 44.7, 44.8, 64.21, 66.8, 131.84, 144.29, 157.92, 160.31, 177.8.

EXAMPLE 4

3-Phenyl-5,5-bis-pyridin-4-ylmethyl-2-thioxo-imidazolidin-4-one

Under a N₂ atmosphere were combined 0.542 g (2.0 mmol) of bispyridylmethyl methylglycinate, 25 mls of EtOH, and 0.26 ml (2.2 mmol) of phenylisothiocyanate and the resultant solution was allowed to reflux for 48 hours. The reaction was then cooled, concentrated and the product purified via column chromatography on silica gel (95/5 EtOAc/MeOH) to yield 0.652 g (86.9%) of the title compound as a white solid.

¹H NMR (DMSO): 3.18 (d-2H), 3.34 (d-2H), 6.21-6.24 (m-2H), 7.22 (d4H), 7.31–7.33 (m-3H), 8.54 (d-4H), 10.9 (s-1H).
¹³C NMR (DMSO): 41.03, 69.09, 125.29, 127.56, 128.79, 132.32, 142.88, 149.48, 173.63, 180.91.

EXAMPLE 5

3-Methyl-2-(2-adamantyl)-sulfanyl-5,5-bis-pyridin-4-ylmethyl-3.5-dihydrolmidazol-4-one A. 3-(1-adamantyl)-5,S-bisipyridinylmethyl-2-thioxo-imidazolidin-4-one Under a nitrogen (N₂) atmosphere in EtOH (25 mls) were combined 1.084 g. (4 mmol) of bispyridylmethyl methylg-lycinate 4 and excess 1-adamantyl isothiocyanate (1.54 g, 8 mmol). The reaction mixture was heated to reflux and allowed to stir for 144 hours. The reaction mixture was allowed to cool, was concentrated in vacuo and crude product was purified by column chromatography (silica gel, 9:1 EtOAc/MeOH) to afford 0.557 g (32.2%) of the title compound, which was isolated as a crystalline solid from ethyl acetate/hexane (EtOAc/Hex).

¹H NMR (DMSO): 1.45 (bs-6H), 1.86 (bs-3H), 2.05 (d-6H), 2.98 (d-2H), 3.12 (d-2H), 7.14 (d-4H), 8.48 (d4H), 10.35 (s-1H).
¹³C NMR (DMSO): 28.88, 35.21, 38.65, 41.14, 61.71, 66.54, 125.11, 142.74, 149.11, 175.8, 182.46.

B. 3-(1-Adamantyl-2-methyl)-sulfanyl-5,5-bis-pyridin-4-ylmethyl-3.5-dihydro-imidazol-4-one Under a N₂ atmosphere in 50 ml of acetone were combined 0.432 g (1 mmol) of bispyridylmethyl N-1-adamantyl thiohydantoin, 0.138 g (1 mmol) of potassium carbonate and 0.142 g (1 mmol) of methyl iodide and the reaction mixture was allowed to stir at room temperature for 48 hours. The reaction mixture was concentrated in vacuo and partitioned in 100 ml EtOAc/10 ml H₂O. The organic layer was separated, washed with H₂O(4×10 ml), brine (1x), dried over NaSO₄ and concentrated in vacuo. The crude product was purified via column chromatography (silica gel: 92.5/7.25 EtOAc/MeOH) and crystallized from isopropyl ether/hexane (IPE/Hex) to yield N-1-adamantylimidazolinone ¹³C NMR (CDCl₃): 15.28, 29.48, 35.6, 39.55, 42.7, 60.35, 74.38, 125.4, 144.23, 149.05, 162.83, 182.66.

EXAMPLE 6

3-Methyl-5.5-bis-pyridin-4-ylmethyl-2-thioxo-imidazolidin-4-one

Under a N₂ atmosphere in 15 ml of EtOH were combined 0.65 g (2.4 mmol) of bispyridylmethyl methylglycinate 4 and 1.5 g (20.5 mmol) of methylisothiocyanate and the reaction mixture was heated at reflux for 72 hours at which point 15 mg of KCN were added and the reaction was heated for 6 additional hours. The reaction mixture was then cooled and placed directly on a silica gel column and eluted with 9:1 EtOAc/Hex to yield 0.74 g of the title compound as light tan solids after trituration from EtOAc/Hex, m.p. 225°–227° C.

¹H NMR (DMSO): 2.55(s-3H), 3.07(d-2H), 3.23(d-2H), 7.12(d4H), 8.46(d4H), 10.61 (s-1 H).
¹³C NMR (DMSO): 26.13, 40.81, 68.52, 125, 142.77, 149.3, 174.24, 181.45.

EXAMPLE 7

3-Methyl-2-(2-adamantyl)-sulfanyl-5,5-bis-pyridin-4-ylmethyl-3.5-dihydro-imidazol-4-one Under a N₂ atmosphere in dimethylformamide (DMF) (8 mls) were combined 0.624 g, (2 mmol) of 3-methyl-5,5-bis-pyridin-4-ylmethyl-2-thioxo-imidazolidin-4-one 0.276 g (2 mmol) of potassium carbonate (K₂CO₃) and 0.43 g (2 mmol) of 2-bromoadamantane. The reaction mixture was heated to a gentle reflux, allowed to stir for 48 hours, was cooled and then partitioned between 125 ml EtOAc and 50 ml H₂O. The organic extract was washed with H₂O (3×25 ml), brine (1x), dried over Na₂SO₄, filtered, concentrated and chromato-graphed on silica gel using 9:1 EtOAc/MeOH to yield 0.522 g of the title compound which was crystallized from Et₂O/Hex, m.p. 156.5–158.

Anal. calc. for C₂₆H₃₀N₄OS: C, 69.92; H, 6.77; N, 12.55. Found: C, 70.04; H, 6.43; N, 12.50.

¹H NMR (CDCl₃): 1.62–1.97 (m-15H), 2.49 (s-3H), 3.03–3.12 (m4H), 4.25 (s-1H), 7.15 (d4H), 8.41 (d-4H).
¹³C NMR (CDCl₃): 25.87, 26.96, 27.26, 32.89, 33.48, 37.32, 38.48, 42.2, 52.51, 75.43, 125.31, 144.3, 149.17, 161.47, 181.51.

EXAMPLE 8

1-Adamantan-1-yl-3.3-bis-pyridin4-ylmethyl-pyrrolidine-2.5-dione

A. Bispyridylmethyl diethylmalonate

Under a N₂ atmosphere in 50 ml of absolute EtOH was added 1.55 g (67.4 mmol) of freshly shaved sodium metal. The mixture was stirred until all of sodium metal was dissolved. Then 10.1 ml (67.4 mmol) of diethylmalonate was added dropwise and the resultant solution was allowed to stir for 1 hour. Then 8.6 g (67.4 mmol) of freshly prepared 4-picolyl chloride was added over a three minute period. The reaction mixture initially turned pale green and then cloudy as a sodium chloride precipitate was formed. The reaction mixture was allowed to stir for two additional hours and was then refluxed for three hours and finally allowed to stir at room temperature overnight. The crude reaction was quenched in 500 ml ethyl acetate (EtOAc) and 250 ml water (H₂O) and the aqueous layer was separated and extracted with 200 ml of fresh EtOAc. The organic extracts were combined, washed with H₂O(3×250 ml) and brine (1x) and dried over Na₂SO₄, filtered and concentrated in vacuo to yield 15.5 g of a light pink oil which NMR showed to be the expected mixture of starting diethylmalonate and mono and bis alkylated products. This mixture was purified by chromatography on silica gel starting out with EtOAc as solvent to yield 7.11 g of mono alkylated product as a colorless oil followed by 4:1 ethyl acetate/methanol to yield 5.37 g of the desired Bispyridylmethyl diethylmalonate as a pale yellow oil.

¹H NMR (CDCl₃): 1.12 (t-3H), 3.16 (s-4H), 4.1 (q-4H), 7.05 (d-4H), 8.49 (d-4H).

¹³C NMR (CDCl₃): 13.82, 38.99, 59.04, 61.81, 125.25, 145.08, 149.72, 169.97.

Mono alkylated material can be conveniently recycled to the desired bis alkylated material. 4-Picolyl chloride free base was prepared fresh using following procedure: 4-picolyl chloride HCl was dissolved in H₂O, an equal volume of CH₂Cl₂ was added and enough concentrated ammonium hydroxide (NH₄OH) was added to raise the pH to greater than 10. The CH₂Cl₂ layer was then separated and dried over Na₂SO₄ with stirring until the CH₂Cl₂ layer was sparkling clear. The organic extract was filtered, concentrated in vacuo and pumped down on hi-vac until a steady weight was reached and used immediately.

B. Bispyridylmethyl malonic acid, di-sodium salt

To a solution of 4.0 g (100 mmol) of NaOH in 125 ml of H₂O was added a solution of 13.0 g (38 mmol) of bispyridylmethyl diethylmalonate in 100 ml of THF and 25 ml of methanol (MeOH). The resultant solution was allowed to stir at ambient temperature for 48 hours and was then concentrated in vacuo to provide oily solids which were chased with ethanol (EtOH) (3×100 ml). The resultant white solids were slurried with 350 ml of EtOH for 72 hours, were filtered and washed well first with EtOH and then with diethyl ether. The product was finally dried under N₂ to yield 8.6 g (69.4%) of desired product.

C. Methyl-3-pyridin4-yl-2-pyridin-4-ylmethyl-propionic acid

To 40 ml of cold MeOH at 0° C. was added slowly 5 mls of acetylchloride and the resultant solution was allowed to stir for 5 min. Then 2.2 g (6.6 mmol) of bispyridylmethyl-malonic acid di-sodium salt was added and the reaction mixture was heated to reflux for 18 hours. The reaction mixture was then cooled, concentrated in vacuo and the residue was dissolved in 20 ml of H₂O and made basic with sodium bicarbonate (NaHCO₃). The solution was then saturated with sodium chloride (NaCl) and extracted with CH₂Cl₂ (2×20 ml). The extracts were dried, concentrated in vacuo to yield 1.22 g of the title compound as a viscous oil which was good enough to use as is or could be purified further via vacumn distillation.

¹H NMR (CDCl₃): 2.71–2.79 (m-2H), 2.89–3.02 (m-3H), 3.47 (s-3H), 7.03 (d-4H), 8.46(d4H).

¹³C NMR (CDCl₃): 37.38, 47.48, 51.81, 124.12, 147.43, 150.04, 174.02.

D. N-Adamantan-1-yl-2-bromo-acetamide

To an anhydrous toluene solution (25 ml) at 0° C. containing 1-adamantanamine (4.445 g, 29.39 mmol) and tri-ethylamine (4.92 ml, 35.27 mmol) under a nitrogen atmosphere was added dropwise with stirring a solution of bromoacetyl bromide (2.56 ml, 29.39 mmol in 10 ml of toluene). The solution was warmed to ambient temperature and stirred for 2.5 hours. The triethylamine (TEA) salts were filtered and washed with toluene. The filtrate was extracted with 1 M HCl and brine, dried (Na₂SO₄) and concentrated in vacuo to yield 5.74 g (71%) of the title compound as a light brown solid which was crystallized from ether/hexane.

E. 1-Adamantan-1-yl-3,3-bis-pyridin-4-ylmethyl-pyrrolidine-2.5-dione

To a distilled THF solution (30 ml) at −78° C. under a nitrogen atmosphere containing diisopropylamine (1.13 ml, 8.032 mmol distilled from sodium metal) was added butyl-lithium (BuLi) (8.032 mmol). The solution was allowed to warm to approximately −25° C., recooled to −78° C. and stirred for 1 hour. The lithium diisopropylamide (LDA) solution was added (via cannula) to a separate flask containing 3-pyridin4-yl-2-pyridin-4-ylmethyl-propionic acid ethyl ester (2.056 g, 8.032 mmol) in THF (30 ml) at −78° C. The red mixture was allowed to warm to approx. −25° C., recooled to −78° C., and stirred for 1 hour. To this lithium enolate solution was added (via cannula) a solution of N-adamantan-1-yl-2-bromo-acetamide (2.186 g, 8.032 mmol) in THF (10 ml) at −78° C. The mixture was kept at −78° C. for 16 hours, warmed to ambient temperature and stirred for two additional hours. The mixture was quenched with EtOAc, washed with an equal volume of H₂O and brine, dried (Na₂SO₄) and concentrated in vacuo to a brown oil. The crude mixture was chromatographed on silica gel (1:1 acetone:hexane) to afford 475 mg (14%) of the title compound as a white solid, which was recrystallized from isopropyl ether, mp 137°–138.5° C.

¹H NMR (CDCl₃): 1.59–1.61 (m, 7H), 2.00-2.02 (m, 8H), 2.40 (s, 2H), 2.67 (d,, 2H), 3.23 (d, 2H), 7.06 (m, 4H), 8.51 (m, 4H) ppm.

¹³C NMR (CDCl₃): 29.67, 36.05, 36.24, 39.10, 43.25, 47.96, 61.77, 125.46, 144.29, 150.26, 175.45, 181.26 ppm.

Analysis: Calc. for C₂₆H₂₉N₃O₂: C, 75.15: H, 7.03; N, 10.11. Found: C, 75.22; H, 7.32; N, 9.89.

EXAMPLE 9

N-adamantan-1-yl-4-hydroxy-2.2-bis-pyridin-4-ylmethyl-butyramide

Under a N₂ atmosphere was combined 1-adamantan-1-yl-3,3-bis-pyridin-4-ylmethyl-pyrrolidine-2,5-dione (0.5 g, 1.2 mmol) and 20 ml of isopropyl alcohol. To this solution was added a large excess of sodium borohydride (1.0 g, 26.3 mmol) and the suspension was stirred for eleven days. The reaction was then quenched in a 2:1 mixture of EtOAc/H₂O, the organic layer was separated, the aqueous layer was extracted (1×EtOAc), and then the organic layers were combined, washed 4×25 ml H₂O, 1× brine, dried over Na₂SO₄, filtered and concentrated to yield 0.35 g of gum which contained a mixture of products. This mixture was placed on a silica gel column and eluted using 85:15 EtOAc/MeOH to yield first 62 mg of the minor alcohol product, which required further purification (silica gel chromatography, 95:5 CH₂Cl₂/MeOH) and resulted in a final yield of 38 mg, 7.5%, of clean material, and 0.22 g (43.5%) of the title compound as white solids that required no further purification.

¹H NMR (CDCl₃): 1.55–1.6 (m-8H), 2.0 (s-3H), 2.65 (d-2H), 3.22 (d-2H), 3.87 (t-2H), 5.93 (s-1H), 7.12 (d4H), and 8.37 (d-4H).

¹³C NMR (CDCl₃) 29.32, 34.34, 36.21, 41.3, 42.8, 50.65, 52.51, 57.86, 125.82, 146.63, 149.26, 172.55.

EXAMPLE 10

1-Adamantan-1-yl 3.3-bis-pyridin-4-ylmethyl-pyrrolidine-2-one

Under N₂ atmosphere were combined N-adamantan-1-yl-4-hydroxy-2,2-bis-pyridin4-ylmethyl-butyramide (50 mg, 0.24 mmol), triphenylphosphine (63 mg, 0.24 mmol), and diisopropylazodicarboxylate (0.047 ml, 0.24 mmol) in 5 ml THF and the resulting solution was allowed to stir for 18 hours. The reaction mixture was then placed directly on a silica gel column and eluted with 85:15 mix of EtOAc/MeOH to yield 46 mg of product as a gum which in turn could be crystallized from isopropylether/hexane to yield the desired product as a white solid, m.p. 163.5°–165° C.

$^1$H NMR (CDCl$_3$): 1.67 (s-6H), 1.9-1.93 (m-8H), 2.05 (s-3H), 2.69 (d-2H), 3.1 (d-2H), 3.42 (t-2H), 7.18 (d4H), and 8.49 (d4H).

$^{13}$C NMR (CDCl$_3$): 29.99, 36.86, 43.0, 44.73, 49.23, 54.51, 66.18, 126.07, 146.63, 149.65, 160.45.

EXAMPLE 11

3-Adamantan-1-yl 5.5-bis-furan-3-ylmethyl-1-methyl-imidazolidine-2.4-dione

Under a N$_2$ atmosphere was combined 3-adamantan-1-yl 5,5-bis-furan-3-ylmethyl-imidazolidine-2,4-dione (0.100 g, 0.25 mmol) in 2 ml of dry THF. To this solution was added a 60% dispersion of sodium hydride (11.1 mg, 0.28 mmol) and the suspension was allowed to stir for 1.5 hours. To this reaction mixture was then added methyl iodide (32 μl, 0.508 mmol) and the reaction mixture was allowed to stir for 30 minutes and quenched with water and extracted with 2×30 ml of methylene chloride (CH$_2$Cl$_2$). The organic layer was separated, dried over MgSO$_4$, filtered and concentrated in vacuo to yield 0.103 g of the title compound.

$^1$H NMR (CDCl$_3$): 1.23–2.10 (m-15H), 2.84 (d, J=12.5 Hz-2H), 2.88 (s-3H), 2.96 (d, J=12.2 Hz-2H), 6.15 (s-2H), 7.19 (s-2H), 7.30 (s-2H).

$^{13}$C NMR (CDCl$_3$): 24.73, 29.59, 30.06, 36.08, 39.45, 67.34, 111.18, 117.47, 140.77, 143.08, 156.2, 175.21.

EXAMPLE 12

1-Adamantan-1-yl-3-(furan-3-ylmethyl)-3-(pyridin4-ylmethyl)-pyrrolidine-2.5-dione

A. 3-Furan-3-yl-2-pyridin-4-ylmethyl propionic acid ethyl ester

Under a nitrogen atmosphere were combined diethyl-2-furanylmethyl-2-pyridylmethylmalonate (5.80 g, 17.5 mmol) (prepared by a standard alkylation of diethyl pyridylmethyl malonate and 3-bromomethylfuran) and lithium chloride (1.48 g, 35.0 mmol) in dimethylsulfoxide (DMSO) (10 mls) containing 315 μl of H$_2$O. The mixture was heated under reflux for 2 hours. The reaction was cooled, quenched with EtOAc/H$_2$O and the organic layer was separated, washed with H$_2$O(3X), brine, dired over Na$_2$SO$_4$ filtered and concentrated in vacuo. The residue was chromatographed (1:1 hexane:EtOAc) on silica gel to afford a 4:1 mixture of the title compound and starting malonate.

B. 1-Adamantan-1-yl-3-(furan-3-ylmethyl)-3-(pyridin-4-ylmethyl)-pyrrolidine-2.5-dione Under a nitrogen atmosphere were combined diisopropylamine (2.72 ml, 6.79 mmol) and anhydrous THF (30 mls), and the solution was cooled to –78° C. 2.5M butyl lithium (2.72 ml, 6.79 mmol) was added and the solution was allowed to warm to about 3-furan-3-yl-2-pyridin4-ylmethyl propionic acid ethyl ester (2.20 g (80% pure), 6.79 mmol) was added dropwise and the solution was stirred at –78° C. for 1 hour. To this solution was added 1.85 g (6.79 mmol) of N-adamantyl-1-yl-2-bromo-acetamide at –78° C. and the mixture was kept at –78° C. for 16 hours and then warmed to room temperature for 3 hours. The standard reaction workup after silica gel chromatography (1:1 EtOAC:hexane) provided 300 mg of the title compound.

$^1$H NMR (CDCl$_3$): 1.20–2.20 (m-13H), 2.38 (m-2H), 2.78 (dd-2H), 2.92 (dd-2H), 6.19 (s-1H), 7.02 (d-2H), 7.20 (d-1H), 7.29 (s-1H), 8.45 (d-2H).

The compounds of Examples 13–126 which appear in the chart below, were also prepared by the methods described in this application. In the chart, the following abbreviations are used: Bn=benzyl, NAPTH=naphthyl, ADM=adamantyl, FUR=furyl, 5-HT=serotonin, DA=dopamine, ACh=acetylcholine, PYR=pyridinyl, Me=methyl, THF=tetrahydrofuryl, cPr=cyclopropyl, Et=ethyl, Ph=phenyl, iPr=isopropyl, c-hex=cyclohexane, and c-oct=cyclooctane.

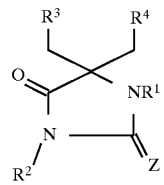

| Example | R$^2$ | R$^3$ | R$^4$ | Z | R$^1$ |
|---|---|---|---|---|---|
| 13 | 1-ADM | 3-PYR | 3-PYR | S | H |
| 14 | Me | 3-PYR | 3-PYR | S | H |
| 15 | 1-ADM | 3-PYR | 3-PYR | O | H |
| 16 | 1-ADM | Ph | p-NO$_2$Ph | O | H |
| 17 | 1-ADM | Ph | p-NH$_2$Ph | O | H |
| 18 | 1-ADM | 3-FUR | 3-FUR | O | H |
| 19 | 1-ADM | 3-thiophenyl | 3-thiophenyl | O | H |
| 20 | 1-ADM | 3-THF | 3-THF | O | H |
| 21 | 1-ADM | 3-FUR | 3-FUR | O | Me |
| 22 | 1-ADM | 3-PYR | 3-PYR | O | Me |
| 23 | 1-ADM | 4-PYR | 4-PYR | O | Bn |
| 24 | 1-ADM | 4-PYR | H | O | H |

-continued

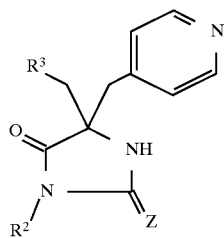

| | | | | Estimated (%) | | | Found (%) | | | |
|---|---|---|---|---|---|---|---|---|---|---|
| Example | R² | R³ | Z | C | H | N | C | H | N | Melting Point (°C.) |
| 25 | 1-ADM | 3-PYR | S | 69.41 | 6.52 | 12.95 | | | | |
| 26 | 1-ADM | 2-PYR | S | 69.41 | 6.52 | 12.95 | | | | |
| 27 | 1-ADM | p-NO₂Ph | O | 67.81 | 6.13 | 12.17 | 67.46 | 6.07 | 12.17 | |
| 28 | 1-ADM | p-NH₂Ph | O | 72.53 | 7.02 | 13.01 | | | | |
| 29 | 1-ADM | p-(NHCOMe)Ph | O | 66.07 | 6.53 | 11.01 | | | | 164 |
| 30 | 1-ADM | 3-FUR | O | 71.09 | 6.71 | 10.36 | | | | |
| 31 | 1-ADM | Ph | O | 75.15 | 7.03 | 10.11 | | | | 134–135 |
| 32 | 1-ADM | 3-PYR | O | 72.09 | 6.78 | 13.45 | | | | |
| 33 | 1-ADM | 2-PYR | O | | | | | | | |

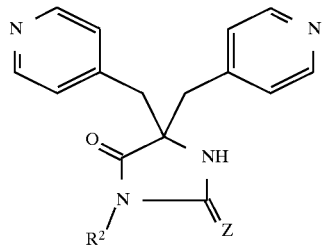

| | | | Estimated (%) | | | Found (%) | | | |
|---|---|---|---|---|---|---|---|---|---|
| Example | R² | Z | C | H | N | C | H | N | Melting Point (°C.) |
| 34 | Ph | O | 70.38 | 5.06 | 15.63 | | | | 237–238 |
| 35 | Ph | S | 67.36 | 4.84 | 14.96 | | | | 228.5–230 |
| 36 | c-Hex | O | 69.21 | 6.64 | 15.37 | 68.87 | 6.47 | 15.34 | |
| 37 | c-Hex | S | 66.29 | 6.36 | 14.72 | 66.11 | 6.37 | 14.35 | 263–264 |
| 38 | 1-ADM | O | 72.09 | 6.78 | 13.45 | | | | |
| 39 | 1-ADM | S | 69.25 | 6.45 | 12.66 | 69.41 | 6.52 | 12.95 | |
| 40 | Me | S | 61.51 | 5.16 | 17.94 | | | | |
| 41 | 1-NAPTH | O | 70.89 | 5.49 | 12.72 | 70.78 | 5.01 | 12.49 | |
| 42 | 1-NAPTH | S | 70.73 | 4.75 | 13.20 | | | | 261–262.5 |
| 43 | 2,6-di-iPrPh | S | 70.71 | 6.59 | 12.22 | | | | 299–301 |
| 44 | (−)3-pinaneMe | S | 69.61 | 7.19 | 12.49 | | | | 224.5–226 |
| 45 | (+)3-pinaneMe | S | 69.61 | 7.19 | 12.49 | | | | 225–226 |
| 46 | t-Bu | O | 67.44 | 6.55 | 16.56 | | | | 210.5–211.5 |
| 47 | t-Bu | S | 64.38 | 6.26 | 15.81 | 64.35 | 6.20 | 14.75 | 257.5 |
| 48 | 1-hex | O | 68.82 | 7.15 | 15.29 | 68.77 | 7.00 | 14.96 | 167.5–169 |
| 49 | 1-hex | S | 66.06 | 6.75 | 14.47 | 65.93 | 6.85 | 14.65 | 158.5–160 |
| 50 | c-oct | S | 67.62 | 6.91 | 13.71 | | | | 259–260 |

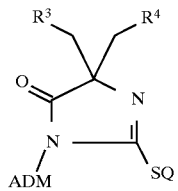

| | | | | Estimated (%) | | | Found (%) | | | |
|---|---|---|---|---|---|---|---|---|---|---|
| | R³ | R⁴ | Q | C | H | N | C | H | N | Melting Point (°C.) |
| 51 | 4-Pyridyl | 4-Pyridyl | Bn | 73.53 | 6.56 | 10.72 | | | | 170.5–172 |
| 52 | 4-Pyridyl | 4-Pyridyl | CH₂COPh | 71.97 | 6.22 | 10.17 | | | | 130–131 |

-continued

| | | | |
|---|---|---|---|
| 53 | 4-Pyridyl | 4-Pyridyl | Et |
| 54 | 4-Pyridyl | 4-Pyridyl | iPr |
| 55 | 4-Pyridyl | 4-Pyridyl | Me |
| 56 | 4-Pyridyl | 2-Pyridyl | Me |
| 57 | 3-Pyridyl | 3-Pyridyl | Me |

| | | | | | | |
|---|---|---|---|---|---|---|
| 55 | 69.92 | 6.77 | 12.55 | 70.07 | 6.61 | 12.67 167.5–169 |
| 57 | 69.92 | 6.77 | 12.55 | | | 169.5–171 |

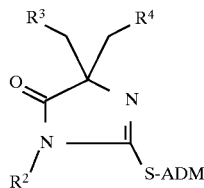

| | | | | Estimated (%) | | | Found (%) | | | |
|---|---|---|---|---|---|---|---|---|---|---|
| | $R^3$ | $R^4$ | $R^2$ | C | H | N | C | H | N | Melting Point (°C.) |
| 58 | 4-Pyridyl | 4-Pyridyl | Ph | | | | | | | |
| 59 | 4-Pyridyl | 4-Pyridyl | t-Bu | | | | | | | |
| 60 | 4-Pyridyl | 4-Pyridyl | Me | 69.92 | 6.77 | 12.55 | 70.04 | 6.43 | 12.50 | |
| 61 | 3-Pyridyl | 3-Pyridyl | Me | 69.92 | 6.77 | 12.55 | 69.78 | 6.60 | 12.10 | |
| 62 | 3-Pyridyl | 4-Pyridyl | Me | 69.92 | 6.77 | 12.55 | | | | 156–158 |
| 63 | 2-Pyridyl | 4-Pyridyl | Me | 69.92 | 6.77 | 12.55 | 69.87 | 6.59 | 12.52 | |
| 64 | 3-Furyl | 4-Pyridyl | Me | | | | | | | |
| 65 | 3-Furyl | 3-Furyl | Me | | | | | | | |

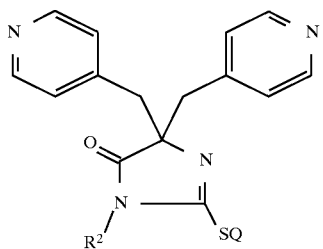

| | $R^2$ | Q |
|---|---|---|
| 66 | Ph | Bn |
| 67 | Ph | Me |
| 68 | Ph | $CH_2CO_2Et$ |
| 69 | Ph | $CH_2COPh$ |
| 70 | Ph | 2-ADM |
| 71 | 1-NAPTH | Me |
| 72 | 2-NAPTH | Me |
| 73 | Me | Bn |
| 74 | Me | 2-ADM |
| 75 | c-hex | Me |
| 76 | c-hex | Bn |
| 77 | Ph | Bn |
| 78 | c-hex | $CH_2COPh$ |
| 79 | c-Hex | $CHPh_2$ |
| 80 | (+)3-pinanemethyl | Bn |
| 81 | (+)3-pinanemethyl | Me |
| 82 | (+)3-pinanemethyl | Me |
| 83 | t-Bu | Me |
| 84 | t-Bu | 2-ADM |
| 85 | c-oct | Me |
| 86 | 1-ADM | Bn |
| 87 | 1-ADM | Me |
| 88 | 1-ADM | iPr |
| 89 | 1-ADM | $CH_2COPh$ |
| 90 | 1-ADM | Et |

-continued

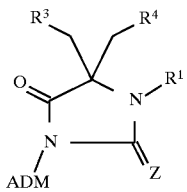

|  | Z | R³ | R⁴ | R¹ | Estimated C | Estimated H | Estimated N | Found C | Found H | Found N | Melting Point (°C.) |
|---|---|---|---|---|---|---|---|---|---|---|---|
| 91 | O | 4-Pyridyl | 4-Pyridyl | H | 70.56 | 6.87 | 13.11 | 70.58 | 6.87 | 12.92 | 284.5–286 |
| 92 | S | 4-Pyridyl | 4-Pyridyl | H | 69.41 | 6.52 | 12.95 | 69.25 | 6.45 | 12.66 | 279–280 |
| 93 | O | 3-Pyridyl | 4-Pyridyl | H | 72.09 | 6.78 | 13.45 |  |  |  |  |
| 94 | S | 3-Pyridyl | 4-Pyridyl | H |  |  |  |  |  |  |  |
| 95 | O | 2-Pyridyl | 4-Pyridyl | H | 72.09 | 6.78 | 13.45 |  |  |  |  |
| 96 | S | 2-Pyridyl | 4-Pyridyl | H | 69.41 | 6.52 | 12.95 |  |  |  |  |
| 97 | O | 3-Pyridyl | 3-Pyridyl | H | 72.09 | 6.78 | 13.45 | 71.99 | 6.51 | 13.41 |  |
| 98 | S | 3-Pyridyl | 3-Pyridyl | H | 61.52 | 5.16 | 17.93 |  |  |  |  |
| 99 | O | 4-Pyridyl | 4-Pyridyl | Me | 72.53 | 7.02 | 13.00 |  |  |  |  |
| 100 | O | 4-NO₂Ph | 4-Pyridyl | H | 67.81 | 6.13 | 12.17 |  |  |  | 220–221 |
| 101 | O | 4-NH₂Ph | 4-Pyridyl | H | 72.53 | 7.02 | 13.01 |  |  |  | 157–158 |
| 102 | O | 4-NH₂Ph | 4-Pyridyl | H | 66.07 | 6.53 | 11.01 |  |  |  |  |
| 103 | O | 3-FUR | 4-Pyridyl | H | 71.09 | 6.71 | 10.36 |  |  |  |  |
| 104 | O | 3-FUR | 3-FUR | H | 70.03 | 6.64 | 7.10 |  |  |  |  |
| 105 | O | 3-FUR | 3-FUR | Me | 70.51 | 6.91 | 6.86 |  |  |  |  |

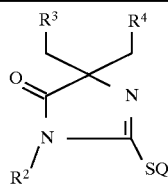

| Example | R² | R³ | R⁴ | Q |
|---|---|---|---|---|
| 106 | 1-ADM | 2-PYR | 4-PYR | Me |
| 107 | Me | 3-PYR | 4-PYR | 2-ADM |
| 108 | Me | 3-PYR | 3-PYR | 2-ADM |
| 109 | 1-ADM | 3-PYR | 3-PYR | Bn |
| 110 | 1-ADM | 3-PYR | 3-PYR | Me |
| 111 | Me | 4-PYR | 3-FUR | 2-ADM |
| 112 | Me | 4-PYR | 2-PYR | 2-ADM |

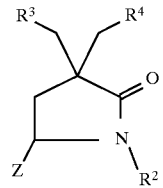

Pyrrolidin-2-ones

|  | R³ | R⁴ | R² | Z |
|---|---|---|---|---|
| 113 | 4-PYR | 4-PYR | 1-ADM | H |
| 114 | 4-PYR | 4-PYR | 1-ADM | OH |
| 115 | 4-PYR | 1-triazolyl | 1-ADM | H |
| 116 | 4-PYR | (CH₂)₄CN | 1-ADM | H |

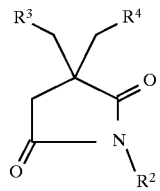

| | $R^3$ | $R^4$ | $R^2$ | Estimated (%) | | | Found (%) | | |
|---|---|---|---|---|---|---|---|---|---|
| | | | | C | H | N | C | H | N |
| 117 | 4-PYR | 4-PYR | 1-ADM | 75.15 | 7.23 | 10.11 | 75.22 | 7.32 | 9.89 |
| 118 | 3-FUR | 3-FUR | 1-ADM | 73.26 | 6.92 | 3.56 | 72.83 | 6.81 | 3.37 |
| 119 | 4-PYR | 3-FUR | 1-ADM | | | | | | |
| 120 | 3-PYR | 3-PYR | 1-ADM | | | | | | |
| 121 | 4-PYR | 4-PYR | 2-ADM | | | | | | |
| 122 | 4-PYR | 4-PYR | Ph | | | | | | |
| 123 | 4-PYR | 4-PYR | c-hex | | | | | | |
| 124 | 4-PYR | 4-PYR | 4-OH-c-hex | | | | | | |
| 125 | 4-PYR | 4-PYR | c-Pr | | | | | | |
| 126 | 4-PYR | 4-PYR | c-oct | | | | | | |

EXAMPLE 127

N-Adamantan-1-yl-2,2-bis-pyridin-4-ylmethyl-malonamic acid methyl ester

To a stirred solution of 3-pyridin4-yl-2-pyridin4-ylmethyl-propionic acid methyl ester (24.44 g, 95 mmol) in tetrahydrofuran (300 ml) chilled with a dry ice/acetone bath, lithium diisopropylamide (70 ml of a 1.5M solution in cyclohexane, 105 mmol of lithium diisopropylamide) was added dropwise over 15 minutes. After stirring for 20 minutes, the solution temperature was elevated to −40° C. After 30 minutes of stirring at −40° C., a solution of adamantyl isocyanate (16.92 g, 95 mmol) in tetrahydrofuran (100 ml) was added dropwise over 10 minutes. After 15 minutes stirring, the cooling bath was removed and the reaction was then stirred for 3 hours at ambient temperature. The reaction was then chilled in an ice water bath and glacial acetic acid (14 ml) was added dropwise over 10 minutes. After stirring for 20 minutes at ambient temperature, the solvent was removed in vacuo, and the residue was extracted into water/methylene chloride (300 ml of each). The aqueous phase was extracted three times with 200 ml portions of fresh methylene chloride. The combined organic extracts were dried (anhydrous sodium sulfate), and concentrated in vacuo to an oil (49.6 g).

Flash chromatography of the entire sample (silica gel, 40 micron mesh; elution initially with acetone/hexanes=3:7 in volume, increasing acetone concentration to, finally, acetone/hexanes=1:1 in volume) afforded an oily solid (16.19 g) which was triturated, first with ethyl acetate/hexanes=5:95 in volume, and then with pure hexanes to afford the title product (14.92 g) as a colorless amorphous solid.

$^{13}$C NMR (CDCl$_3$): 173.66, 166.69, 149.77, 145.05, 124.68, 59.62, 52.29, 52.20, 43.51, 41.12, 36.20, 29.25.

EXAMPLE 128

N-Adamantan-1-yl-2-hydroxymethyl-3-pyridin-4-yl-2-pyridin-4-ylmethyl-propionamide To a well-stirred solution of N-adamantan-1-yl-2,2-bis-pyridin4-ylmethyl-malonamic acid methyl ester (14.92 g, 34 mmol) in methanol (175 ml), sodium borohydride (6.50 g, 172 mmol) was added portionwise over 1 hour (ambient temperature). After stirring at ambient temperature for 18 hours, the solvent was removed in vacuo, and the residue was extracted with aqueous sodium bicarbonate/chloroform (300 ml of each). The aqueous layer was then extracted three times with equal volumes of chloroform. The combined organic extracts were concentrated in vacuo to an oil (13.55 g). Flash chromatography of the entire sample (silica gel, 40 micron mesh; elution with methanol/chloroform=4:96 in volume) afforded the (free base) title compound as an oil (7.9 g).

$^{13}$C NMR (CDCl$_3$) 172.62, 149.17, 146.78, 126.00, 62.39, 51.98, 51.40, 41.49, 40.21, 36.32, 29.39.

EXAMPLE 129

N-Adamantan-1-yl-2-methoxymethyl-3-pyridin-4-yl-2-pyridin4-ylmethyl propionamide To a well-stirred suspension of N-adamantan-1-yl-2-hydroxymethyl-3-pyridin-4-yl-2-pyridin-4-ylmethyl-propionamide (40 mg, 0.1 mmol) in anhydrous tetrahydrofuran (0.50 ml), sodium hydride (7.8 mg of 60% mineral oil dispersion; 0.2 mmol of sodium hydride) was added. After stirring at ambient temperature for 30 minutes, methyl iodide (12.5 μl, 0.2 mmol) was added. After stirring for 2 hours at ambient temperature, the reaction was quenched by the addition of water/methylene chloride (10 ml of each). The mixture was then extracted twice with 10 ml portions of methylene chloride. The combined organic extracts were dried (anhydrous sodium sulfate) and concentrated in vacuo to an oil (60 mg). Flash chromatography of the entire sample (silica gel, 40 micron mesh; elution with methanol/ethyl acetate=1:9 in volume) afforded the title compound (free base) as an amorphous solid (16 mg).

$^{13}$C NMR (CDCl3) 172.03, 149.60, 146.11, 125.77, 72.32, 58.61, 51.83, 51.11, 41.44, 40.29, 36.32, 29.38.

EXAMPLE 130

N-Adamantan-1-yl-2-ethoxymethyl-3-pyridin-4-yl-2-pyridin-4-ylmethyl-propionamide To a well-stirred suspension of N-adamantan-1-yl-2-hydroxymethyl-3-pyridin4-yl-2-pyridin-4-ylmethylpropionamide (40 mg, 0.1 mmol) in anhydrous tetrahydrofuran (0.50 ml), sodium hydride (7.8 mg of 60% mineral oil dispersion; 0.2 mmol of sodium hydride) was added. After stirring at ambient temperature for 15 minutes, ethyl iodide (15.8 µl, 0.20 mmol) was added. After stirring for 2 hours at ambient temperature, the reaction was quenched by the addition of dilute aqueous sodium bicarbonate/methylene chloride (10 ml of each). The mixture was then extracted with three 10 ml portions of methylene chloride. The combined organic extracts were dried (anhydrous sodium sulfate), and concentrated in vacuo to an oil (54 mg). Flash chromatography (silica gel, 40 micron mesh; elution with methanol/ethyl acetate=1:9 in volume) afforded the title compound (free base) (19 mg) as an amorphous solid.

$^{13}$C NMR (CDCl$_3$) 172.23, 171.12, 149.55, 146.22, 125.80, 70.58, 66.74, 51.80, 50.93, 41.44, 40.42, 36.33, 29.38, 15.15.

EXAMPLE 131

N-Adamantan-1-yl-3-oxo-2,2-bis-pyridin-4-ylmethyl-butyramide

To a solution of N-adamantan-1-yl-2,2-bis-pyridin4-ylmethyl-malonamic acid methyl ester (750 mg, 1.68 mmol) chilled to 5° C., cuprous bromide (10.0 mg) and a 3.0M solution of methyl magnesium bromide in diethyl ether (1.67 ml, 5.03 mmol of methyl magnesium bromide) was added. After 18 hours stirring at ambient temperature, a second 1.67 ml portion of 3.0M methyl magnesium bromide in diethyl ether was added. Three hours thereafter, a final 1.67 ml portion of 3.0M methyl magnesium bromide was added. After 18 hours of additional stirring at ambient temperature, the reaction was quenched by addition of 15 ml of ice water containing 250 µl of concentrated sulfuric acid. The mixture was then extracted with three 50 ml portions of methylene chloride. The combined extracts were dried (anhydrous sodium sulfate) and concentrated in vacuo to an oil (520 mg). Flash chromatography of the entire sample (silica gel, 40 micron mesh; elution with methanol/methylene chloride=4:96 in volume) afforded the title compound (free base) as a colorless oil (236 mg).

$^{13}$C NMR (CDCl$_3$) 209.13, 167.60, 149.88, 144.90, 124.62, 63.64, 52.50, 41.17, 40.50, 36.18, 29.28, 27.57.

EXAMPLE 132

N-Adamantan-1-yl-2-formyl-3-pyridin4-yl-2-pyridin-4-ylmethyl-propionamide

To a well-stirred dry ice/acetone bath chilled solution of oxalyl chloride (163 µl, 1.91 mmol) in methylene chloride (4.5 ml), a solution of dimethyl sulfoxide (259 µl, 3.6 mmol) in methylene chloride (2.25 ml) was added dropwise while maintaining the temperature below –55° C. After stirring the reaction at that temperature for 5 minutes, N-adamantan-1-yl-2-hydroxymethyl-3-pyridin-4-yl-2-pyridin-4-ylmethyl-propion-amide (700 mg, 1.73 mmol) in methylene chloride (2.25 ml) was added, and the reaction was stirred for 30 minutes. Triethylamine (1.20 ml, 8.65 mmol) was added, and the reaction was stirred for 5 minutes before removing the cooling bath. After stirring for 20 minutes at ambient temperature, the reaction was quenched by addition to water/methylene chloride (40 ml of each). The mixture was then extracted three times with 40 ml portions of methylene chloride. The combined extracts were dried (anhydrous sodium sulfate) and concentrated in vacuo to afford a yellow oil (1.14 g). Flash chromatography of the entire sample (silica gel, 40 micron mesh; elution initially with methanol/methylene chloride=3:97 in volume, and increasing the methanol concentration during elution finally to methanol/methylene chloride=1:9 in volume) afforded the title compound (475 mg) as an oil.

$^1$H NMR (CDCl$_3$) 1.44–1.74 (m, 12H), 1.84–2.10 (m, 3H), 2.97 (d, 1H), 3.46 (d, 1H), 6.90 (broad s, 1H), 6.98 (d, 4H), 8.42 (d, 4H), 9.65 (s, 1H).

EXAMPLE 133

Racemic 3-hydroxy-2,2-bis-pyridin-4-ylmethyl-pentanoic acid adamantan-1-ylamide

To an ice bath chilled solution/suspension of N-adamatan-1-yl-2-formyl-3-pyridin-4-yl-2-pyridin-4-ylmethyl-propionamide (50 mg, 0.12 mmol) in diethyl ether (0.25 ml), cuprous bromide (2 mg) and a 1.0 M solution of ethyl magnesium bromide in tetrahydrofuran (300 µl, 3.0 mmol of ethyl magnesium bromide) were added. The mixture was then stirred at 5° C. for 10 minutes, and 2 hours at ambient temperature. An identical second portion of Grignard reagent (300 µl of 1.0M ethyl magnesium bromide/tetrahydrofuran) was added, and the reaction was stirred at ambient temperature for 18 hours before being quenched with 20 ml ice water containing 20 µl of concentrated sulfuric acid. The pH was adjusted to 8.0 by addition of sodium bicarbonate. The mixture was then extracted three times with 20 ml portions of methylene chloride. The combined organic extracts were dried (anhydrous sodium sulfate) and concentrated in vacuo to an oil (100 mg). Flash chromatography of the entire sample (silica gel, 40 micron mesh; elution with initially methanol/methylene chloride=4:96 in volume and increasing the methanol concentration during elution finally to 1:9 methanol/methylene chloride in volume) afforded the title compound (free base) (5 mg) as an oil.

$^1$H NMR (CDCl$_3$) δ 1.00 (t, 3H), 1.40-2.20 (m, 2H), 1.70 (m, 6H), 2.00 (m, 6H), 2.10 (m 3H), 2.56 (d, 1H), 2.90–3.05 (m, 2H), 3.08 (s, 2H), 3.30–3.45 (m, 1H), 6.60 (broad s, 1H), 7.10 (d, 2H), 7.16 (d, 2H), 8.50 (d, 4H).

EXAMPLE 134

N-Adamantan-1-yl-3-hydroxy-2.2-bis-pyridin-4-ylmethyl-butyramide

By the method of the previous example, 50 mg (0.12 mmol) of N-adamantan-1-yl-2-formyl-3-pyridin-4-yl-2-pyridin4-ylmethyl-propionamide was converted to the title compound (free base) (9 mg), isolated as an oil.

$^1$H NMR (CDCl$_3$) δ 1.36 (d, 3H), 1.70 (m, 6H), 2.00 (m, 5H), 2.10 (m, 4H), 2.80–3.25 (m, 5H), 3.82 (m, 1H), 6.80 (broad s, 1H), 7.18 (m, 4H), 8.55 (m, 4H).

EXAMPLE 135

1-Adamantan-1-yl-3.3-bis-pyridin-4-ylmethyl-azetidine-2.4-dione

To a solution of N-adamantan-1-yl-2,2-bis-pyridin4-ylmethyl-malonamic acid methyl ester (100 mg, 0.23 mmol) in anhydrous tetrahydrofuran (1.5 ml), a 1.4M solution of methyl magnesium bromide in toluene/ tetrahydrofuran (Aldrich Chemical Co., 330 µl, 0.46 mmol of methyl magnesium bromide) and cuprous bromide (1.6 mg) was added. The reaction was heated at 50° C. for 6 hours and then quenched by addition to 15 ml of ice water containing 200 µl of concentrated sulfuric acid. The pH of the mixture was then adjusted to 8.0 with aqueous sodium bicarbonate. Two 15 ml methylene chloride extractions were combined, dried (anhydrous sodium sulfate), and concentrated in vacuo to an oil (104 mg). Flash chromatography of the entire sample (silica gel, 40 micron mesh; elution with methanol/ methylene chloride=4:96 in volume) afforded the title compound (20 mg) as an oil.

$^{13}$C NMR (CDCl$_3$) δ 170.75, 149.54, 144.06, 125.24, 71.18, 57.84, 39.40, 36.66, 35.44, 28.52.

EXAMPLE 136

N-(1,7,7-trimethyl-bicyclo[2.21]hept-2-yl)-malonamic acid methyl ester

To a well-stirred, ice bath chilled solution of R—(+)-bornylamine (Aldrich Chemical Co., 0.50 g, 3.30 mmol) and triethylamine (0.45 ml, 3.30 mmol) in methylene chloride, methyl malonyl chloride (Aldrich Chemical Co., 0.35 ml, 3.30 mmol) was added dropwise. The reaction was allowed to warm gradually to ambient temperature and to stir for 18 hours at that temperature. After quenching by cautious addition of 15 ml of saturated aqueous bicarbonate, the mixture was extracted with an equal volume of methylene chloride. The organic extract was then washed with an equal volume of water, dried (anhydrous sodium sulfate) and concentrated in vacuo to afford the title compound (0.95 g) as a yellow oil.

EXAMPLE 137

3-Pyridin-4-yl-2-pyridin-4-yl methyl-2-(1,7,7-trimethyl-bicyclo[2.2.1]hept-2-ylcarbamoyl)-propionic acid methyl ester To a solution of N-(1,7,7-trimethyl-bicyclo[2.2.1]hept-2-yl)-malonamic acid methyl ester (0.95 g, 3.7 mmol) in methanol (7 ml), sodium methoxide (0.20 g, 3.7 mmol) was added, and the mixture was stirred for 1 hour at ambient temperature. 4-Picolylchloride (0.53 g, 4.1 mmol of freshly liberated free base from 4-picolyl chloride hydrochloride; Aldrich Chemical Co.) was added, and the reaction was then stirred for 18 hours at ambient temperature. Ethyl acetate and water (15 ml of each) were added, and the mixture was well shaken. The separated aqueous extracted was then extracted with an equal volume portion of fresh ethyl acetate. The combined organic extracts were dried (anhydrous sodium sulfate), and concentrated in vacuo to an orange oil (1.16 g). Flash chromatography of the entire sample (silica gel, 40 micron mesh; elution with initially ethyl acetate and subsequently with methanol/ethyl acetate up to a 1:4 ratio, respectively, in volume) afforded the title compound (12 mg) as an oil.

EXAMPLE 138

2-Hydroxymethyl-3-pyridin-4-yl-2-pyridin-4-methyl-N-(1,7,7-trimethyl-bicyclo[2.2.1 1]hept-2-yl)-propionamide (derived from R—(+)-bornylamine)

To a solution of 3-pyridin-4-yl-2-pyridin-4-ylmethyl-2-(1,7,7-trimethyl-bicyclo[2.2.1]hept-2-carbamoyl)propionic acid methyl ester (12 mg, 0.027 mmol) in methanol (0.5 ml) sodium borohydride (5 mg, 0.13 mmol) was added and the reaction was stirred for 18 hours at ambient temperature. An additional 8 mg (0.21 mmol) of sodium borohydride was added, and the reaction was stirred for 18 additional hours before adding a final 8 mg portion of sodium borohydride. After a final 18 hours stirring, the reaction was quenched by the addition of water/methylene chloride (10 ml of each). The mixture was extracted with four 5 ml portions of methylene chloride, which were combined, extracted with an equal volume of water, dried (anhydrous sodium sulfate), and concentrated in vacuo to afford an 11 mg residue. Flash chroma- tography (silica gel, 40 micron mesh; elution with initially methanol/methylene chloride =4.96 in volume, and increasing the methanol concentration to finally 1:10 respectively during the elution) afforded the title compound (6 mg) as a colorless oil.

EXAMPLE 139

1-Adamantan-1yl-3-pyridin4-ylmethyl-3-pyrimidin-4-ylmethyl-pyrrolidine-2,5-dione, dihydrochloride salt A. Pyridin-4-ylmethyl-pyrimidin-4-ylmethyl diethylmalonate Sodium (0.253 g, 11.0 mmol) was added to absolute ethanol (EtOH) (13 mL) and allowed to dissolve at room temperature. The solution was cooled to 0° C. and a solution of pyridin-4-ylmethyl diethylmalonate (prepared as described in Example 8A) (2.60 g, 10.3 mmol) in EtOH (8 mL) was added dropwise. After 50 min, 4- chloromethylpyrimidine (1.46 g, 11.4 mmol) was added and the resulting mixture was allowed to stir at room temperature overnight (16 hours). The mixture was concentrated and the residue was partitioned between EtOAc and H$_2$O. The organic layer was separated, washed with brine, dried (Na$_2$SO$_4$), filtered, and concentrated. Purification by flash chromatography (EtOAc) gave the title product (2.55 g, 72%) as a clear oil.

$^1$H-NMR (CDCl$_3$) δ 9.00 (S, 1H), 8.64 (d, 1H, J=5.3 Hz), 8.39 (d, 2H, J=6.1 Hz), 7.41 (d, 1H, J=5.2 Hz), 7.18 (d, 2H, J=6.1 Hz), 4.82 (s, 2H), 4.16 (q, 2H, J=7.1 Hz), 3.34 (d, 2H, J=13.2 Hz), 1.13 (t, 3H, J=7.1 Hz).

CIMS m/e (rel intensity) 344 ([M+1]$^+$, 100).

B. 3-Pyridin-4-yl-3-pyrimidin4-ylmethyl propanoic acid, methyl ester

A mixture of diester obtained in step A (1.25 g, 3.64 mmol) and NaOH (0.44 g, 10.92 mmol) in 1:1 MeOH/H$_2$O (10 mL) was heated at 65° C. overnight (16 hours). The mixture was concentrated to a volume of 5 mL, and additional H$_2$O(2 mL) followed by concentrated HCl (0.66 mL) was added. The mixture was stirred at room temperature until evolution of CO$_2$ had subsided (30 min). The reaction was concentrated and a solution of 3% HCl in MeOH (40 mL) was added to the residue. The resulting mixture was heated to reflux for 3 hours. The mixture was concentrated and the residue was purified by flash chromatography (EtOAc to 5% MeOH-EtOAc) to give the title compound (0.624 g, 66%) as a yellow oil.

$^1$H-NMR (D$_2$O) δ 6 8.96 (s,1 H), 8.61 (d,1 H. J=5.3 Hz), 8.37 (d, 2H, J=6.2 Hz), 7.42 (d, 1 H. J=5.3 Hz), 7.25 (d, 2H, J=6.2 Hz), 3.56 (s, 3H), 3.33–3.46 (m, 1 H), 2.91–3.18 (m, 4H).

CIMS m/e (rel intensity) 258 ([M+1]$^+$, 100).

C. 1-Adamantan-1-yl-3-pyridin-4-ylmethyl-3-pyrimidin-4-ylmethyl-pyrrolidine-2,5-dione, dihydrochloride salt.

Freshly prepared 1M LDA (1.29 mL, 1.29 mmol) was added to a cold (−78° C.) solution of the ester obtained in step B (0.30 g, 1.17 mmol) in THF (5 mL). After 30 min, a solution of N-adamantan-1-yl-2-bromoacetamide (prepared as described in Example 8D) (0.32 g, 1.17 mmol) in THF (1.5 mL) was added and the reaction was allowed to stir at room temperature overnight (16 hours). The mixture was partitioned between EtOAc and $H_2O$, and the separated aqueous layer was re-extracted with EtOAc (2x). The combined organic layer was washed with brine, dried ($Na_2SO_4$), filtered, and concentrated. The residue was purified by flash chromatography (40→70% acetone-hexane) and preparative HPLC (Dynamax-60A C18; flow=23 ml/min; solvent A: 50 mM $NH_4OAc$ pH 4.55; solvent B=$CH_3CN$; gradient: 10→60% B over 45 min) to give the title compound, free base (0.031 g, 6.4%) as a clear oil. Addition of ethereal HCl to a solution of free base in $Et_2O$ yielded after concentration the dihydrochloride salt (0.024 g, 66%) as an off-white solid.

mp 134° C. (gums)

$^1$H-NMR (DMSO-$d_6$) δ 9.03 (s, 1 H), 8.88 (d, 2H, J=6.4 Hz), 8.72 (d, 1 H. J=5.1 Hz), 7.94 (d, 2H, J=6.4 Hz), 7.41 (d, 1H, J =5.1 Hz), 3.19–3.32 (m, 3H), 3.04 (d, 1H, J=14.9 Hz), 2.67 (s, 2H), 2.08 (s, 6H), 1.99 (br s, 3H), 1.59 (s, 6H).

CIMS m/e (rel intensity) 417 ([M+1]$^+$, 100).

FABHRMS calc'd for $C_{25}H_{28}N_4O_2$: 416.2302. Found: 416.2242.

EXAMPLE 140

3-N-Adamantan-1-yl-3-oxo-2-pyridin-4-ylmethyl-2-pyrimidin-4-ylmethyl-propanoic acid, ethyl ester, dihydrochloride salt.

A. 3-N-Adamantan-1-yl-3-oxo-propanoic acid, ethyl ester

A solution of ethyl malonyl chloride (10.7 mL, 0.132 mol) in $CH_2Cl_2$ (20 mL) was added dropwise to a cold (0° ) solution of 1-adamantanamine (20.0 g, 0.132 mol) and triethylamine (20.37 mL, 0.146 mol) in $CH_2CL_2$ (200 mL). After addition was complete, the mixture was allowed to stir at room temperature for 30 min. The reaction mixture was washed with $H_2O$, brine, dried ($Na_2SO_4$), filtered, and concentrated to give the crude title compound (33.84 g, 92%) as an off-white solid.

mp 98°–100° C.

$^1$H-NMR (CDCl$_3$) δ 4.18 (q, 2H, J=7.2 Hz), 3.21 (s, 2H), 2.00–2.10 (m, 9H), 1.67 (s, 6H), 1.28 (t, 3H, J=7.1 Hz).

CIMS m/e (rel intensity) 266 ([M+1]$^+$, 100).

B. 3-N-Adamantan-1-yl-3-oxo-2-pyridin-4-ylmethyl-propanoic acid, ethyl ester (a) and 3-N-Adamantan-1-yl-3-oxo-2,2-bis-pyridin-4-ylmethyl-propanoic acid, ethyl ester (b).

A 21% by weight solution of sodium ethoxide in ethanol (68.3 mL, 0.183 mol) was added to a mixture of ester obtained in step A (33.84 g, 0.122 mol) in absolute EtOH (400 mL) at room temperature. After 25 min, a solution of picolyl chloride, free base (18.0 g, 0.141 mol) in absolute EtOH (20 mL) was added. The dark reaction mixture was stirred overnight (16 hours) at room temperature and then heated at 60° C. for 2 h. The mixture was concentrated and the residue was partitioned between EtOAc and $H_2O$. The separated aqueous layer was re-extracted with EtOAc (2x). The combined organic layer was washed with brine, dried ($Na_2SO_4$), filtered, and concentrated. Purification by flash chromatography (EtOAc) gave title compound (a) (8.84 g, 19.4%) as a yellow solid and title compound (b) (19.0 g, 33.3%) as an off-white solid. Title compound (a) was purified further by flash chromatography (30% acetone-hexane) to give pure product (5.16 g, 11.4%) as a white solid.

(a) mp 111°–112° C.

$^1$H-NMR (CDCl$_3$) δ8.50 (d, 2H, J=5.8 Hz), 7.13 (d, 2H, J=5.8 Hz), 5.95 (br s, 1H), 4.074.19 (m, 2H), 3.26–3.38 (m, 1H), 3.09–3.24 (m, 2H), 2.06 (br s, 3H), 1.92–1.94 (m, 6H), 1.64–1.66 (m, 6H), 1.20 (t, 3H, J=7.1 Hz).

CIMS r/e (rel intensity) 357 ([M+1]$^+$, 100).

(b) mp 105°–106° C.

$^1$H-NMR (CDCl$_3$) δ8.48 (d, 2H, J=6.0 Hz), 7.05 (d, 2H, J=6.0 Hz), 4.16 (q, 2H, J=7.2 Hz), 3.57 (d, 2H, J=12.9 Hz), 3.10 (d, 2H, J=12.9 Hz), 2.03 (br s, 3H), 1.81–1.83 (m, 6H), 1.62–1.64 (m, 6H), 1.36 (t, 3H, J=7.1 Hz).

CIMS m/e (rel intensity) 448 ([M+1]$^+$, 100).

C. 3-N-Adamantan-1-yl-3-oxo-2-pyridin-4-ylmethyl-2-pyrimidin-4-ylmethyl-propanoic acid, ethyl ester, dihydrochloride salt.

The same procedure described in step B was followed with a solution of ester obtained in step B (a) (0.50 g, 1.40 mmol) in EtOH (6 mL), a 21% by weight solution of sodium ethoxide in ethanol (0.575 mL, 1.54 mmol), and a solution of 4-chloromethyl-pyrimidine (0.198 g, 1.54 mmol) in EtOH (1.5 mL) except that the reaction mixture was stirred at room temperature only overnight (16 hours). Purification by flash chromatography (EtOAc) gave the title compound, free base (0.327 g, 52%) as a yellow foam. Addition of ethanolic HCl to a solution of the free base (0.116 g, 0.26 mmol) in $Et_2O$/EtOH yielded after concentration and trituration with $Et_2O$ the dihydrochloride salt (0.95 g, 70%) as an off-white solid.

mp>140° C. (dec)

$^1$H-NMR (DMSO-$d_6$) δ9.1 (d, 1 H. J=0.9 Hz), 8.85 (d, 2H, J=6.5 Hz), 8.72 (d, 1 H. J=5.2 Hz), 7.90 (d, 2H, J=6.4 Hz), 7.49 (s, 1 H), 7.40 (dd, 1 H. J=5.0 Hz, J=1.1 Hz), 4.08 (q, 2H, J=6.9 Hz), 3.52 (AB q, 2H, J =13.3 Hz), 3.32 (s, 2H), 1.98 (br s, 3H), 1.84 (s, 6H), 1.59 (s, 6H), 1.10 (t, 3H, J=7.0 Hz).

CIMS m/e (rel intensity) 449 ([M+1]$^+$, 100).

EXAMPLE 141

N-Adamantan-1-yl-3-hydroxy-2-pyridin-4-ylmethyl-2-pyrimidin-4-ylmethyl-propanamide, dihydrochloride salt.

Sodium borohydride (NaBH$_4$) (0.103 g, 2.72 mmol) was added to a solution of 3-N-adamantan-1-yl-3-oxo-2-pyridin4-ylmethyl-2-pyrimidin-4-ylmethyl-propanoic acid, ethyl ester (prepared as described in Example 140) (0.061 g, 0.136 mmol) in MeOH (5 mL) at room temperature. Additional NaBH$_4$ (0.052–0.103 g, 1.36-2.72 mmol) was added each time at 1 h intervals until small amounts or no starting material could be detected by TLC (EtOAc). The reaction mixture was slowly poured over $H_2O$ and extracted with EtOAc. The separated aqueous layer was re-extracted with EtOAc (2x).

The combined organic layer was washed with brine, dried (Na$_2$SO$_4$), filtered, and concentrated. Purification by flash chromatography (1 to 5% MeOH-$CH_2Cl_2$) afforded the title compound, free base (0.032 g, 58%) as a yellow foam. Addition of ethanolic HCl to a solution of the free base in EtOH yielded after concentration and trituration with $Et_2O$ the dihydrochloride salt (0.023 g, 61%) as an off-white solid.

mp 152°–154° C. (dec)

$^1$H-NMR (DMSO-d$_6$) δ9.10 (s, 1H), 8.84 (d, 2H, J=6.3 Hz), 8.71 (d, 1H, J=5.0 Hz), 7.98 (d, 2H, J=6.4 Hz), 7.40 (d, 1 H. J=4.8 Hz), 7.34 (s, 1 H), 3.40–3.55 (m, 2H), 3.22 (AB q, 2H, J=12.6 Hz), 3.00 (AB q, 2H, J =13.5 Hz), 1.99 (br d, 3H), 1.87 (s, 20 6H), 1.60 (s, 6H).

CIMS m/e (rel intensity) 407 ([M+1]$^+$, 100).

Anal. Calc'd for C$_{24}$H$_{30}$N$_4$O$_2$2HCl H$_2$O: C, 57.95; H, 6.89; N, 11.26. Found: C, 57.87; H, 7.15; N, 11.36.

EXAMPLE 142

3-N-Adamantan-2-yl-3-oxo-2-pyridin-4-ylmethyl-2-pyrimidin-4-ylmethyl-propanoic acid, ethyl ester, dihydrochloride salt.

The procedure described in Example 140B was followed with a solution of 3-N-adamantan-2-yl-3-oxo-2-pyridin4-ylmethyl-propanoic acid, ethyl ester (0.750 g, 2.10 mmol) in EtOH (9 mL), a 21% by weight solution of NaOEt in EtOH (0.863 mL, 2.31 mmol), and 4-chloromethylpyrimidine (0.297 g, 2.31 mmol) except that the reaction was heated at 60° C. overnight (16 hours). The title compound, free base (0.571 9, 61%) was obtained as an off-white foam. A portion of the free base (0.119 g, 0.27 mmol) was treated with ethanolic HCl as described in Example 140C to give the dihydrochloride salt (0.103 g, 74%) as a light yellow solid.

mp 154°–156° C. (dec)

$^1$H-NMR (DMSO-d$_6$) δ9.01 (s, 1H), 8.82 (d, 2H, J=6.5 Hz), 8.70 (d, 1H, J=5.2 Hz), 8.28 (d, 1 H, J=7.3 Hz), 7.77 (d, 2H, J=6.5 Hz), 7.39 (d, 1 H. J =5.2 Hz), 4.09 (q, 2H, J=7.0 Hz), 3.70–3.77 (m, 1H), 3.54 (s, 2H), 3.47 (s, 2H), 1.55–1.78 (m, 12H), 1.36–1.48 (m, 2H), 1.07 (t, 3H, J=7.0 Hz).

CIMS m/e (rel intensity) 449 ([M+1]$^+$, 100).

EXAMPLE 143

N-Adamantan-2-yl-3-hydroxy-2-pyridin-4-ylmethyl-2-pyrimidin4-4ylmethyl-propanamide, dihydrochloride salt.

The procedure described in Example 141 was followed with the free base of 3-N-adamantan-2-yl-3-oxo-2-pyridin4-ylmethyl-2-pyrimidin4-ylmethyl-propanoic acid, ethyl ester (prepared as described in Example 142) (0.214 g, 0.477 mmol) in MeOH (10 mL) to give the title compound (0.066 9, 29%) as an off-white solid.

mp 138°–140° C. (dec)

$^1$H-NMR (DMSO-d$_6$) 69.07 (s, 1 H), 8.82 (d, 2H, J=6.4 Hz), 8.69 (d, 1 H, J=5.2 Hz), 7.94 (d, 2H, J=6.5 Hz), 7.37 (d, 1 H, J=5.2 Hz), 3.81 (br d, 1 H, J=6.2 Hz), 3.64 (d, 1H, J=11.1 Hz), 3.46 (d, 1H, J=10.9 Hz), 3.33 (d, 1H, J=12.6 Hz), 3.18 (d, 1H, J=12.6 Hz), 3.12 (d, 1H, J=13.7 Hz), 2.96 (d, 1H, J=13.6 Hz), 1.60–1.83 (m, 12H), 1.39–1.50 (m, 2H).

CIMS m/e (rel intensity) 407 ([M+1]$^+$, 100).

Anal. Calc'd for C$_{24}$H$_{30}$N$_4$O$_2$●2HCl●0.5H$_2$0: C, 59.02 H, 6.81; N, 11.47. Found: C, 59.13; H, 7.15; N, 11.29.

EXAMPLE 144

3-N-Adamantan-1-yl-3-oxo-2-pyrimidin-4-ylmethyl-propanoic acid, ethyl ester (a) and 3-N-Adamantan-1-yl-3-oxo-2,2-bis-pyrimidin-4-ylmethyl-propanoic acid, ethyl ester, dihydrochloride salt (b).

The procedure described in Example 140B was followed with a solution of 3-N-adamantan-1-yl-3-oxo-propanoic acid, ethyl ester (prepared as described in Example 140A) (1.13 g, 4.25 mmol) in EtOH (7 mL), a 21% by weight solution of NaOEt in EtOH (2.06 mL, 5.53 mmol), and 4-chloromethylpyrimidine (0.60 g, 4.67 mmol) except that the reaction was stirred at room temperature only overnight (16 hours). Purification by flash chromatography (EtOAc to 5% MeOH-EtOAc) gave title compound (a) (0.497 g, 33%) and title compound (b), free base (0.381 g, 20%) as a yellow foam. A portion of title compound (b), free base (0.185 g, 0.41 mmol) was treated with ethanolic HCl as described in Example 140C to give the dihydrochloride salt (b) (0.179 g, 83%) as a yellow solid.

(a) $^1$H-NMR (CDCl$_3$) δ9.08 (s, 1 H), 8.72 (d, 1 H, J=5.3 Hz), 7.27 (d, 1 H, J=5.3 Hz), 6.02 (br s, 1 H), 4.07–4.23 (m, 2H), 3.86 (t, 2H, J=7.2 Hz), 3.35 (d, 2H, J=7.2 Hz), 2.05 (br s, 3H), 1.92–1.94 (m, 6H), 1.65–1.67 (m, 6H), 1.24 (t, 3H, J=7.1 Hz).

CIMS m/e (rel intensity) 358 ([M+1]$^+$, 100).

(b) mp 115°–117° C. (dec)

1H-NMR (DMSO-d$_6$) δ9.06 (s, 2H), 8.70 (d, 2H, J=5.2 Hz), 7.51 (s, 1 H), 7.43 (d, 2H, J=5.2 Hz), 4.04 (q, 2H, J=7.1 Hz), 3.40 (AB q, 4H, J =14.7 Hz), 1.97 (br s, 3H), 1.81 (s, 6H), 1.58 (s, 6H), 1.04 (t, 3H, J=7.1 Hz).

CIMS m/e (rel intensity) 450 ([M+1]$^+$, 100).

EXAMPLE 145

N-Adamantan-1-yl-3-hydroxy-2,2-bis-pyrimidin-4-yl methyl-propanamide, dihydrochloride salt.

The procedure described in Example 141 was followed with the free base of 3-N-adamantan-1-yl-3-oxo-2,2-bis-pyrimidin4-ylmethyl-propanoic acid, ethyl ester (prepared as described in Example 144) (0.175 9, 0.389 mmol) in MeOH (7 mL) to give after flash chromatography (5% MeOH-EtOAc) and salt formation the title compound (0.080 g, 43%) as an off-white solid.

mp >120° C. (dec)

$^1$H-NMR (DMSO-d$_6$) δ9.10 (s, 2H), 8.70 (d, 2H, J=5.2 Hz), 7.47 (d, 2H, J=5.2 Hz), 7.38 (s, 1H), 3.55 (s, 2H), 3.13 (d, 2H, J =13.6 Hz), 3.00 (d, 2H, J=13.6 Hz), 1.97 (br s, 3H), 1.85 (s, 6H), 1.59 (s, 6H).

CIMS r/e (rel intensity) 408 ([M+1]$^+$, 100).

Anal. Calc'd for C$_{23}$H$_{29}$N$_5$O$_2$●2HCl●1.75H$_2$O: C, 53.96; H, 6.79; N, 13.67. Found: C, 54.01; H, 7.16; N, 13.46.

EXAMPLE 146

3-N-Adamantan-1-yl-3-oxo-2-pyridin-3-ylmethyl-2-pyrimidin-4-ylmethyl-propanoic acid, ethyl ester, dihydrochloride salt.

The procedure described in Example 140B was followed with a solution of 3-N-adamantan-1-yl-3-oxo-2-pyrimidin4-ylmethyl-propanoic acid, ethyl ester [prepared as described in Example 144] (0.225 g, 0.629 mmol) in EtOH (3 mL), a 21% by weight solution of NaOEt in EtOH (0.306 mL, 0.818 mmol), and a solution of 3-chloromethylpyridine (0.088 g, 0.692 mmol) in EtOH (1 mL) except that the reaction was heated at 60° C. overnight (16 hours). After flash chromatography (75 to 100% EtOAc-hexane), the title compound, free base (0.119 g, 42%) was obtained as a yellow solid. A portion of the free base (0.039 g, 0.087 mmol) was treated with ethanolic HCl as described in Example 140C to give the dihydrochloride salt (0.030 g, 66%) as a light yellow solid.

mp >170° C. (dec)

$^1$H-NMR (DMSO-d$_6$) δ9.09 (s, 1H), 8.85 (d, 1H, J =5.3 Hz), 8.77 (s, 1H), 8.72 (d, 1H, J=5.1 Hz), 8.44 (d, 1H, J=8.3

Hz), 8.04 (dd, 1H, J =7.9 Hz, J=5.7 Hz), 7.49 (s, 1 H), 7.41 (d, 1 H, J=5.1 Hz), 4.07 (q, 2H, J =7.1 Hz), 3.28–3.53 (m, 4H), 1.98 (br s, 3H), 1.82 (s, 6H), 1.58 (s, 6H), 1.08 (t, 3H, J =7.2 Hz).

CIMS m/e (rel intensity) 449 ([M+1]$^+$, 100).

Anal. Calc'd for $C_{26}H_{32}N_4O_3$●2HCl: C, 59.88; H, 6.57; N, 10.74. Found: C, 60.26; H, 6.99; N, 10.81.

EXAMPLE 147

N-Adamantan-1-yl-3-hydroxy-2-pyridin-3-ylmethyl-2-pyrimidin-4-ylmethyl-propanamide, dihydrochloride salt.

The procedure described in Example 141 was followed with the free base of 3-N-adamantan-1-yl-3-oxo-2-pyridin-3-ylmethyl-2-pyrimidin4-ylmethyl-propanoic acid, ethyl ester (prepared as described in Example 146) (0.075 g, 0.167 mmol) in MeOH (3.5 mL) to give the title compound (0.034 g, 42%) as an off-white solid.

mp 162°–164° C. (dec)

$^1$H-NMR (DMSO-d$_6$) 69.09 (s, 1H), 8.81 (d, 1H, J =5.4 Hz), 8.77 (s, 1H), 8.69 (d, 1H, J=5.1 Hz), 8.50 (d, 1H, J=8.1 Hz), 8.02 (dd, 1H, J =7.8 Hz), 7.39 (d, 1H, J=4.7 Hz), 7.29 (s, 1 H), 3.35–3.51 (m, 2H), 3.13 (AB q, 2H, J =13.4 Hz), 2.98 (AB q, 2H, J=13.7 Hz), 1.97 (br s, 3H), 1.84 (s, 6H), 1.58 (s, 6H).

CIMS m/e (rel intensity) 407 ([M+1]$^+$, 100).

Anal. Calc'd for $C_{24}H_{30}N_4O_2$●2HCl-1.5H$_2$0: C, 56.92; H, 6.97; N,11.06. Found: C, 57.10; H, 6.96; N, 11.01.

EXAMPLE 148

3-N-Adamantan-2-yl-3-oxo-2-pyrazol-1-ylmethyl-2-pyridin-4-ylmethyl-propanoic acid, ethyl ester, dihydrochloride salt.

The procedure described in Example 140B was followed with a solution of 3-N-adamantan-1-yl-3-oxo-2-pyridin-4-ylmethyl-propanoic acid, ethyl ester (prepared as described in Example 140B) (0.500 g, 1.40 mmol) in EtOH (6 mL), a 21% by weight solution of NaOEt in EtOH (0.681 mL, 1.82 mmol), and a solution of 1-chloromethylpyrazole (0.180 g, 1.54 mmol) in EtOH (1.5 mL) except that the reaction was stirred at room temperature only overnight (16 hours). After flash chromatography (20% acetone-hexane), the title compound, free base (0.208 g, 34%) was obtained as a clear oil which crystallized from hexane. A portion of the free base (0.053 g, 0.12 mmol) was treated with ethanolic HCl as described in Example 140C to give the dihydrochloride salt (0.035 g, 56%) as a white solid.

mp 143°–146° C. (dec)

$^1$H-NMR (DMSO-d$_6$) δ8.87 (d, 2H, J =6.4 Hz), 8.01 (d, 2H, J=6.5 Hz), 7.61 (d, 1H, J=2.2 Hz), 7.53 (d, 1H, J=1.7Hz), 6.27 (t, 1H, J =2.0Hz), 4.59 (AB q, 2H, J=14.6 Hz), 4.08–4.17 (m, 2H), 3.55 (d, 1H, J =13.4 Hz), 3.42 (d, 1H, J=13.9 Hz), 2.00 (br s, 3H), 1.87 (s, 6H), 1.60 (s, 6H), 1.18 (t, 3H, J=7.2 Hz).

CIMS m/e (rel intensity) 437 ([M+1]$^+$, 100).

EXAMPLE 149

N-Adamantan-1-yl-3-hydroxy-2-pyrazol-1-ylmethyl-2-pyridin-4-ylmethyl-propanamide, dihydrochloride salt.

The procedure described in Example 141 was followed with the free base of 3-N-adamantan-1-yl-3-oxo-2-pyrazol-1-ylmethyl-2-pyridin-4-ylmethyl-propanoic acid, ethyl ester (prepared as described in Example 148) (0.147 g, 0.377 mmol) in MeOH (7 mL) to give after flash chromatography (EtOAc5% EtOAc-MeOH) the title compound (0.091 g, 58%) as a white solid.

mp >120° C. (gums)

$^1$H-NMR (DMSO-d$_6$) δ8.85 (d, 2H, J=6.3 Hz), 8.01 (d, 2H, J=6.5 Hz), 7.63 (d,1 H, J=2.1 Hz), 7.48 (d, 1 H. J=1.7 Hz), 7.41 (s, 1 H), 6.27 (t, 1 H. J =2.0 Hz), 4.44 (d, 1H, J=14.2 Hz), 4.28 (d, 1H, J=14.3Hz), 3.45 (d, 1H, J=11.2Hz), 3.27 (d, 1H, J=11.2 Hz), 3.10–3.15 (m, 2H), 1.99 (br s, 3H), 1.89 (s, 6H), 1.60 (s, 6H).

CIMS m/e (rel intensity) 395 ([M+1]$^+$, 100).

EXAMPLE 150

3-N-Adamantan-1 yl-2-furan-3-ylmethyl-3-oxo-2-pyridin-4-ylmethyl-propanoic acid, ethyl ester, hydrochloride salt.

The procedure described in Example 140B was followed with a solution of 3-N-adamantan-1-yl-3-oxo-2-pyridin-4-ylmethyl-propanoic acid, ethyl ester (prepared as described in Example 140B) (0.50 g, 1.40 mmol) in EtOH (7 mL), a 21% by weight solution of NaOEt in EtOH (0.681 mL, 1.82 mmol), and a solution of 3-bromomethylfuran (0.248 g, 1.54 mmol) in EtOH (1.5 mL) except that the reaction was stirred at room temperature only overnight (16 hours). The title compound, free base (0.147 9, 24%) was obtained as a clear oil. A portion of the free base (0.070 g, 0.16 mmol) was treated with ethanolic HCl as described in Example 140C to give the hydrochloride salt (0.026 g, 34%) as a light yellow solid.

mp >100° C. (gums)

$^1$H-NMR (DMSO-d6) δ8.76 (d, 2H, J=6.0 Hz), 7.67 (d, 2H, J =6.1 Hz), 7.60 (s,1 H), 7.48 (s,1 H), 7.39 (s, 1 H), 6.28 (s,1 H), 4.08 (q, 2H, J=7.1 Hz), 3.32 (AB q, 2H, 13.6 Hz), 3.01 (s, 2H), 2.00 (br s, 3H), 1.87 (s, 6H), 1.60 (s, 6H), 1.16 (t, 3H, J=7.1 Hz).

CIMS m/e (rel intensity) 437 ([M+1]$^+$, 100).

Anal. Calc'd for $C_{26}H_{32}N_2O_4$●HCl●H$_2$O: C, 63.60; H, 7.18; N, 5.70. Found: C, 20 63.55; H, 7.22; N, 5.65.

EXAMPLE 151

N-Adamantan-1-yl-2-furan-3-ylmethyl-3-hydroxy-2-pyridin-4-ylmethyl-propanamide, hydrochloride salt.

The procedure described in Example 141 was followed with the free base of 3-N-adamantan-1-yl-2-furan-3-ylmethyl-3-oxo-2-pyridin-4-ylmethyl-propanoic acid, ethyl ester (prepared as described in Example 150) (0.075 g, 0.172 mmol) in MeOH (5 mL) to give after flash chromatography (75% EtOAc-hexane) and salt formation the title compound (0.021 g, 28%) as a white solid.

mp >120° C. (gums)

$^1$H-NMR (DMSO-d$_6$) δ8.77 (d, 2H, J=5.9 Hz), 7.76 (d, 2H, J =6.1 Hz), 7.55 (d, 1H, J=1.6 Hz), 7.39 (s, 1H), 7.19 (s, 1H), 6.31 (d, 1H, J =1.3 Hz), 3.32 (s, 2H), 3.17 (d, 1H, J=12.6 Hz), 2.97 (d, 1H, J =12.6 Hz), 2.81 (d, 1H, J=14.0 Hz), 2.54 (d, 1H, J =14.0 Hz), 2.00 (br s, 3H), 1.91 (s, 6H), 1.61 (s, 6H).

CIMS m/e (rel intensity) 395 ([M+1]$^+$, 100).

Anal. Calc'd for $C_{24}H_{30}N_2O_3$●HCl●H$_2$0: C, 64.20; H, 7.41; N, 6.24. Found: C, 64.00; H, 7.58; N, 6.08.

EXAMPLE 152

3-N-Adamantan-2-yl-2-(3.5-dimethyl)isoxazol-4-ylmethyl-3-oxo-2-pyridin-4-yl-propanoic acid, ethyl ester, hydrochloride salt.

The procedure described in Example 140B was followed with a solution of 3-N-adamantan-1-yl-3-oxo-2-pyridin4- ylmethyl-propanoic acid, ethyl ester (prepared as described in Example 140B) (0.50 g, 1.40 mmol) in EtOH (5 mL), a 21% by weight solution of NaOEt in EtOH (0.58 mL, 1.54 mmol), and 4-chloromethyl-3,5-dimethylisoxazole (0.224 g, 1.54 mmol) except that the reaction was stirred at room temperature only overnight (16 hours). After flash chromatography (20 to 50% acetone-hexane), the title compound, free base (0.409 g, 63%) was obtained as a yellow oil. A portion of the free base (0.182 g, 0.39 mmol) was treated with ethanolic HCl as described in Example 140C to give the hydrochloride salt (0.196 g, 93%) as a yellow solid.

mp 92°–94° C.

$^1$H-NMR (CDCl$_3$) δ8.70 (d, 2H, J=6.0 Hz), 7.90 (s, 1H), 7.75 (d, 2H, J=5.9 Hz), 4.17–4.22 (m, 2H), 3.87 (d, 1H, J=13.0 Hz), 3.31 (d, 1H, J =13.1 Hz), 3.15 (d, 1H, J=14.7 Hz), 2.97 (d, 1H, 14.7 Hz), 2.30 (s, 3H), 2.16 (s, 3H), 2.04 (m, 3H), 1.81 (m, 6H), 1.64 (m, 6H), 1.32 (t, 3H, J=7.2 Hz).

CIMS m/e (rel intensity) 466 ([M+1]$^+$, 100).

Anal. Calc'd for C$_{27}$H$_{35}$N$_3$O$_4$●HCl: C, 64.59 H, 7.23; N, 8.37. Found: C, 64.42; H, 7.55; N, 8.34.

EXAMPLE 153

N-Adamantan-1-yl-2-(3,5-dimethyl)isoxazol-4-ylmethyl-3-hydroxy-2-pyridin-4-ylmethyl-propanamide, hydrochloride salt.

Lithium aluminum hydride (LiAlH$_4$) (0.017 g, 0.44 mmol) was added to a solution of 3-N-adamantan-1-yl-2-(3,5-dimethyl)isoxazol4-ylmethyl-3-oxo-2-pyridin4-ylmethyl-propanoic acid, ethyl ester (prepared as described in Example 152) (0.156 g, 0.36 mmol) in THF (5 mL) at 0° C. After 15 min, sodium sulfate decahydrate (excess) was added slowly and the mixture was allowed to stir at room temperature. The reaction was filtered through a Celite pad (EtOAc wash) and the filtrate was concentrated. The residue was purified by radial chromatography (Chromatroton 1→5% MeOH—CH$_2$Cl$_2$) to give after salt formation as described in Example 140C the title compound (0.114 g, 68%) as a white solid.

$^1$H-NMR (CDCl$_3$) δ8.57 (br d, 2H, J=5.5 Hz), 7.98 (br d, 2H, J=5.5 Hz), 6.46 (s, 1H), 3.62 (d, 1H, J=12.2Hz), 3.54 (s, 2H), 2.93 (d, 1H, J=14.7Hz), 2.83 (d, 1H, J=12.2 Hz), 2.61 (d, 1H, J=14.7 Hz), 2.41 (s, 3H), 2.26 (s, 3H), 2.04 (br s, 3H), 1.85 (m, 6H), 1.64 (m, 6H).

CIMS m/e (rel intensity) 424 ([M+1]$^+$, 100).

Anal. Calc'd for C$_{25}$H$_{33}$N$_3$O$_3$●HCl●1.5H$_2$O: C, 61.65; H, 7.66 N, 8.62 Found: C, 61.99; H, 7.95; N, 8.51.

EXAMPLE 154

3-N-Adamantan-1-yl-3-oxo-2 pyridin4-ylmethyl-2-triazol1-ylmethyl-propanoic acid, ethyl ester, dihydrochloride salt.

The procedure described in Example 140B was followed with a solution of 3-N-adamantan-1-yl-3-oxo-2-pyridin4-ylmethyl-propanoic acid, ethyl ester (prepared as described in Example 140B) (0.50 g, 1.40 mmol) in EtOH (5 mL), a 21% by weight solution of NaOEt in EtOH (0.58 mL, 1.54 mmol), and a solution of 1-chloromethyltriazole (0.181 g, 1.54 mmol) in EtOH (1 mL). After flash chromatography (40% acetone-hexane), the title compound, free base (0.168 g, 27%) was obtained as a white foam. A portion of the free base (0.051 g, 0.12 mmol) was treated with ethanolic HCl as described in Example 140C to give the dihydrochloride salt (0.055 g, 92%) as a white solid.

mp 78°–80° C.

$^1$H-NMR (DMSO-d6) δ8.89 (d, 2H, J=6.4 Hz), 8.47 (s, 1H), 8.08 (s, 1 H), 7.98 (d, 2H, J=6.4 Hz), 7.52 (s, 1H), 4.68 (AB q, 2H, J =14.2 Hz), 4.10–4.15 (m, 2H), 3.55 (AB q,2H, J=14.5 Hz), 1.99(br s,3H), 1.87(s,6H), 1.60(s,6H), 1.18(t, 3H, J=7.0 Hz).

CIMS m/e (rel intensity) 438 ([M+1]$^+$, 100).

EXAMPLE 155

N-Adamantan-1-yl-3-hydroxy-2-pyridin-4-ylmethyl-2-triazol-1-ylmethyl-propanamide, dihydrochloride salt.

The procedure described in Example 141 was followed with the free base of 3-N-adamantan-1-yl-3-oxo-2-pyridin-4-ylmethyl-2-triazol-1-ylmethyl-propanoic acid, ethyl ester (prepared as described in Example 154) (0.210 g, 0.48 mmol) in MeOH (10 mL) to give the title compound (0.076 g, 34%) as a white solid.

mp 80°–82° C.

$^1$H-NMR (DMSO-d$_6$) δ8.86 (d, 2H, J=6.5 Hz), 8.47 (s, 1 H), 8.07 (s, 1H), 7.97 (d, 2H, J=6.5 Hz), 7.36 (s, 1H), 4.54 (d, 1H, J =14.5 Hz), 4.36 (d, 1H, J=14.3 Hz), 3.48 (d, 1H, J=12.6 Hz), 3.31 (d, 1H, J=12.6 Hz), 3.20 (AB q, 2H, J =14.2 Hz), 1.99 (br s 3H), 1.88 (s, 6H), 1.60 (s, 6H).

CIMS n/e (rel intensity) 396 ([M+1]$^+$, 100).

Anal. Calc'd for C$_{22}$H$_{29}$N5O●2HCl●H$_2$O: C, 54.32; H, 6.894 N, 14.40. Found: C, 54.56; H, 6.72; N, 14.49.

EXAMPLE 156

3-N-Adamantan-1-yl-2-(3-methyl)isoxazol-5-ylmethyl-3-oxo-2-pyridin-4-ylmethyl-propanoic acid, ethyl ester, hydrochloride salt.

The procedure described in Example 140B was followed with a solution of 3-N-adamantan-1-yl-3-oxo-2-pyridin4-ylmethyl-propanoic acid, ethyl ester (prepared as described in Example 140B) (0.50 g, 1.40 mmol) in EtOH (5 mL), a 21% by weight solution of NaOEt in EtOH (0.78 mL, 2.10 mmol), and a solution of 5-chloromethyl-3-methylisoxazole (0.203 g, 1.54 mmol) in EtOH (1 mL) except that the reaction was heated at 60 ° C. for 2 hours. After flash chromatography (20% acetone-hexane), the title compound, free base (0.343 g, 54%) was obtained as a clear oil. A portion of the free base (0.095 g, 0.21 mmol) was treated with ethanolic HCl as described in Example 2C to give the hydrochloride salt (0.097 g, 88%) as a white solid.

mp 78°–80° C.

$^1$H-NMR (CDCl$_3$) δ8.69 (br s, 2H), 7.72 (br s, 2H), 7.42 (s, 1H), 5.90 (s, 1H), 4.18–4.36 (m, 2H), 3.72 (d, 1H, J=14.2 Hz), 3.55 (d, 1H, J =15.7 Hz), 3.38 (d, 1H, J =15.7 Hz), 3.31 (d, 1H, J=14.2 Hz), 2.26 (s, 3H), 2.05 (br s, 3H), 1.85 (s, 3H), 1.64 (s, 3H), 1.32 (t, 3H, J=6.9 Hz).

CIMS m/e (rel intensity) 452 ([M+1]$^+$, 100).

Anal. Calc'd for C$_{26}$H$_{33}$N$_3$O$_4$●HCl●H$_2$O: C, 61.71 H, 7.17 N, 8.30. Found: C, 61.35; H, 7.51; N, 7.99.

EXAMPLE 157

N-Adamantan-1-yl-3-hydroxy-2-(3-methyl)isoxazol-5ylmethyl-2-pyridin-4-ylmethyl-propanamide, hydrochloride salt.

The procedure described in Example 141 was followed with the free base of 3-N-adamantan-1-yl-2-(3-methyl)isoxazol-5-ylmethyl-3-oxo-2-pyridin4-ylmethyl-propanoic acid, ethyl ester (prepared as described in Example 156)

(0.25 g, 0.56 mmol) in MeOH (10 mL) to give after chromatography (EtOAc) and salt formation the title compound (0.104 g, 39%) as an off-white solid.

mp 105°–107° C.

$^1$H-NMR (DMSO-d$_6$) δ8.82 (d, 2H, J=6.4 Hz), 7.82 (d, 2H, J =6.5 Hz), 7.27 (s, 1H), 6.05 (s, 1H), 3.37 (s, 2H), 3.21 (d, 1H, J =14.2 Hz), 3.05–3.13 (m, 2H), 2.95 (d, 1 H. J=14.2 Hz), 2.17 (s, 3H), 2.00 (br s, 3H), 1.90 (s, 6H), 1.61 (s, 6H).

CIMS n/e (rel intensity) 410 ([M+1]$^+$, 100).

EXAMPLE 158

3-N-Adamantan-1-yl-3-oxo-2-pyrazin-2-ylmethyl-2-pyridin-4-ylmethyl-propanoic acid, ethyl ester, dihydrochloride salt.

The procedure described in Example 140B was followed with a solution of 3-N-adamantan-1-yl-3-oxo-2-pyridin-4-ylmethyl-propanoic acid, ethyl ester (prepared as described in Example 140B) (0.50 g, 1.40 mmol) in EtOH (5 mL), a 21% by weight solution of NaOEt in EtOH (0.78 mL, 2.10 mmol), and a solution of 2-chloromethylpyrazine (0.396 g, 3.08 mmol) in EtOH (1 mL) except that the reaction was heated at 60° C. overnight (16 hours). After purification by flash chromatography (50→100% EtOAc-hexane), the title compound, free base (0.15 g, 24%) was obtained as a light brown foam. A portion of the free base (0.049 g, 0.11 mmol) was treated with ethanolic HCl as described in Example 140C to give the dihydrochloride salt (0.053 g, 92%) as a light brown solid.

mp 75°–77° C.

$^1$H-NMR (DMSO-d$_6$) δ8.86 (d, 2H, J=6.5 Hz), 8.59 (dd, 1H, J =2.6 Hz, J=1.6 Hz), 8.54 (d, 1H, J=2.6 Hz), 8.52 (d, 1H, J=1.4 Hz), 7.92 (d, 2H, J =6.6 Hz), 4.08 (q, 2H, J=7.1 Hz), 3.51 (AB q, 2H, J=13.2 Hz), 3.35 (AB q, 2H, J =14.7 Hz), 1.99 (br s, 3H), 1.84 (s, 6H), 1.59 (s, 3H), 1.11 (t, 3H, J=7.1 Hz).

CIMS r/e (rel intensity) 449 ([M+1]$^+$, 100).

EXAMPLE 159

N-Adamantan-1-yl-3-hydroxy-2-pyrazin-2-ylmethyl-2-pyridin-4-ylmethyl-2-propanamide, dihydrochloride salt.

The procedure described in Example 141 was followed with the free base of 3-N-adamantan-1-yl-3-oxo-2-pyrazin-2-ylmethyl-2-pyridin-4-ylmethyl-propanoic acid, ethyl ester (prepared as described in Example 158) (0.107 g, 0.24 mmol) in MeOH (5 mL) to give the title compound (0.069 g, 60%) as an off-white solid.

mp 72°–74° C.

$^1$H-NMR (DMSO-d$_6$) δ8.84 (d, 2H, J=6.6 Hz), 8.56 (dd, 1 H, J =2.5 Hz, J=1.5 Hz), 8.52 (d, 1 H. J=1.5 Hz), 8.49 (d, 1 H. J =2.6 Hz), 7.97 (d, 2H, J =6.6 Hz), 7.32 (s, 1H), 3.41–3.45 (m, 2H), 3.28 (d, 1H, J =12.6 Hz), 3.15 (d, 1H, J=12.8 Hz), 3.02–3.08 (m, 2H), 1.99 (br s, 3H), 1.85 (s, 6H), 1.59 (s, 6H).

CIMS m/e (rel intensity) 407 ([M+1]$^+$, 100).

Anal. Calc'd for $C_{24}H_{30}N_4O_2$•2HCl•1.5H$_2$0: C, 56.91 H, 6.96; N, 11.06. Found: C, 57.06; H, 7.35; N, 11.01.

EXAMPLE 160

3-N-Adamantan-1-yl-3-oxo-2,2-bis-pyridin-4-ylmethyl-propanoic acid, 1.1-dimethylethyl ester, dihydrochloride salt.

A. 3-N-Adamantan-1-yl-3-oxo-propanoic acid, 1,1-dimethylethyl ester.

A freshly made 1M solution of lithium diisopropylamide (9.47 mL, 9.47 mmol) was added to a cold (−78° C.) solution of tert-butyl acetate (1.00 g, 8.61 mmol) in THF (20 mL). After 5 min, a solution of 1-adamantyl isocyanate (1.53 g, 8.61 mmol) in THF (7 mL) was added and the mixture was allowed to stir overnight at room temperature. The mixture was partitioned between EtOAc and H$_2$O. The separated aqueous layer was re-extracted with EtOAc (2x). The combined organic layer was washed with brine, dried (Na$_2$SO$_4$), filtered, and concentrated. The yellow waxy solid obtained was triturated with hexane to give the title compound (1.58 g, 62%) as a white powder.

$^1$H-NMR (CDCl$_3$) δ3.12 (s, 2H), 2.00–2.10 (m, 9H), 1.68 (s, 6H), 1.47 (s, 9H).

CIMS m/e (rel intensity) 293 ([M+1]$^+$, 100).

B. 3-N-Adamantan-1-yl-3-oxo-2,2-bis-pyridin-4-ylmethyl-propanoic acid, 1,1dimethylethyl ester, dihydrochloride salt.

A 1M solution of KO'Bu in 'BuOH (0.442 mL, 0.442 mmol) was added to a solution of ester obtained in step A (0.10 g, 0.34 mmol) in 'BuOH (5 mL) at room temperature. After 10 min, a solution of picolyl chloride, free base (0.048 g, 0.374 mmol) in 'BuOH (1 mL) was added. The reaction mixture was stirred for 4 hours at room temperature. The mixture was concentrated and the residue was partitioned between EtOAc and H$_2$O. The separated aqueous layer was re-extracted with EtOAc (2x). The combined organic layer was washed with brine, dried (Na$_2$SO$_4$), filtered, and concentrated. Purification by flash chromatography (EtOAc to 5% MeOH-EtOAc) gave the title compound (0.013 g, 16%) as a clear oil. The free base was treated with ethanolic HCl as described in Example 140C to give the dihydrochloride salt (0.010 g, 5.3%) as a white solid.

mp>165° C.

$^1$H-NMR (CDCl$_3$) δ8.82 (d, 4H, J=6.0 Hz), 7.77 (d, 4H, J =5.8 Hz), 7.54 (s, 1 H), 3.48 (s, 4H), 2.02 (br s, 3H), 5.01 (s, 6H), 1.62 (s, 6H), 1.28 (s, 9H).

CIMS m/e (rel intensity) 476 ([M+1]$^+$, 100).

EXAMPLE 161

3-N-Adamantan-1-yl3-oxo-2,2-bis-pyrimidin-4-ylmethyl-propanoic acid, 1.1 -dimethylethyl ester, dihydrochloride salt The same procedure described in Example 160 was followed with a solution of 3-N-adamantan-1-yl-3-oxo-propanoic acid, 1,1-dimethylethyl ester (0.50 g, 1.70 mmol) in 'BuOH (10 mL), a 1M solution of KO'Bu in 'BuOH (2.21 mL, 2.21 mmol), and a solution of 4-chloromethylpyrimidine (0.240 g,1.87 mmol) in 'BuOH (1.5 mL). The title compound (0.039 g, 9%) was obtained as an off-white solid.

mp 120°–122° C. (dec)

$^1$H-NMR (DMSO-d$_6$) δ9.06 (d, 2H, J =1.1 Hz), 8.71 (d, 2H, J=5.2 Hz), 7.45 (dd, 2H, J=5.2 Hz), 3.38 (AB q, 4H, J=14.8 Hz), 1.99 (br s, 3H), 1.85 (s, 6H), 1.59 (s, 6H), 1.29 (s, 9H).

CIMS m/e (rel intensity) 478 ([M+1]$^+$, 100).

EXAMPLE 162

3-N'-Adamantan-1-yl-3-oxo-2,2-bis-pyridin-4-ylmethyl-N,N-dimethylpropanamide, dihydrochloride salt.

A 2M solution of dimethylamine in THF (2.34 mL, 4.68 mmol) was added to a 1.88M solution of n-BuLi in hexane (2.49 mL, 4.68 mmol) at 0° C. After 5 min, a solution of 3-N-adamantan-1-yl-3-oxo-2,2-bis-pyridin-4-ylmethyl-propanoic acid, ethyl ester (prepared as described in Example 140B) (1.00 g, 2.23 mmol) in THF (6 mL) was added dropwise and the reaction was allowed to stir at room temperature. After 20 min, the reaction was poured over 5% HCl (50 mL). The pH was adjusted to 7 by addition of 40% NaOH and the mixture was extracted with $CH_2Cl_2$ (2x). The organic layer was dried ($Na_2SO_4$), filtered, and concentrated. The residue was purified by flash chromatography (40 to 100% acetone-hexane) to give the title compound (free base) (0.174 g, 17%) as an off-white solid. The free base was treated with ethanolic HCl as described in Example 140C to give the dihydrochloride salt (0.170 g, quantitative) as an off-white solid.

mp 294°–296° C. (dec)

$^1$H-NMR (DMSO-$d_6$) δ8.78 (d, 4H, J=5.8 Hz), 7.78 (d, 4H, J=6.0 Hz), 7.57 (s, 1 H), 3.63 (d, 2H, J=13.0 Hz), 3.39 (d, 2H, J =13.0 Hz), 2.91 (s, 3H), 2.85 (s, 3H), 1.99 (br s, 3H), 1.88 (s, 6H), 1.59 (s, 6H).

CIMS m/e (rel intensity) 447 ([M+1]$^+$, 100).

EXAMPLE 163

2-Hydroxymethyl-3-pyridin-4-yl-2-pyridin-4-methyl-N-(1,7,7-trimethyl-bicyclo[2.2.1]hept-2-yl)-propionamide (derived from R—(+)-bornylamine)

A. 3-Pyridine-4-yl-2-pyridin-4-ylmethyl-2-(1,7,7-trimethyl-bicyclo[2.2.1]hept-2-ylcarbamoyl)-propionic acid methyl ester To a solution of N-(1,7,7-trimethyl-bicyclo[2.2.1]hept-2-yl)-malonamic acid methyl ester (0.95 g, 3.7 mmol) in methanol (7 ml), sodium methoxide (0.20 g, 3.7 mmol) was added, and the mixture was then stirred for 1 hour at ambient temperature. 4-Picolychloride (0.53 g, 4.1 mmol of freshly liberated free base from 4-picolyl chloride hydrochloride; Aldrich Chemical Co.) was added, and the reaction was then stirred for 18 hours at ambient temperature. Ethyl acetate and water (15 ml of each) were added, and the mixture was well shaken. The separated aqueous extracted was then with an equal volume portion of fresh ethyl acetate. The combined organic extracts were dried (anhydrous sodium sulfate), and concentrated in vacuo to an orange oil (1.16 g). Flash chromatography of the entire sample (silica gel, 40 micron mesh; elution with initially ethyl acetate and subsequently with methanol/ethyl acetate up to 1:4 ration, respectively, in volume) afforded the title compound (12 mg) as an oil.

B. 2-Hydroxymethyl-3-pyridin-4-yl-2-pyridin-4-methyl-N-(1,7,7-trimethyl-bicyclo[2.2.1]hept-2-yl)-propionamide (derived from R-(+)-bornylamine)

To a solution of 3-pyridin-4-yl-2-pyridin-4-ylmethyl-2-(1,7,7-trimethyl-bicyclo[2.2.1]hept-2-carbamoyl)propionic acid methyl ester (12 mg, 0.027 mmol) in methanol (0.5 ml) sodium borohydride (5 mg, 0.13 mmol) was added, and the reaction was then stirred for 18 hours at ambient temperature. An additional 8 mg (0.21 mmol) of sodium borohydride was added, and the reaction was stirred for 18 additional hours before adding a final 8 mg portion of sodium borohydride. After a final 18 hours stirring the reaction was quenched by the addition of water/methylene chloride (10 ml of each). The mixture was extracted with four 5 ml portions of methylene chloride, which were combined, extracted with an equal volume of water, dired (anhydrous sodium sulfate), and concentrated in vacuo to afford an 11 mg residue. Flash chromatography (silica gel, 40 micron mesh; elution with initially methanol/methylene chlorid= 4.96 in volume, and increasing the methanol concentration to finally 1:10 respectively during the elution) afforded the title compound (6 mg) as a colorless oil.

Mass spectrum: m/z 408 (M$^+$).

We claim:

1. A compound of the formula

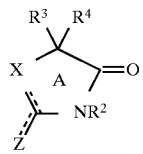    IA

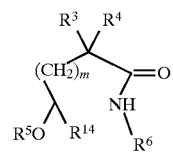    IB

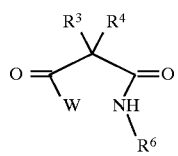    IC

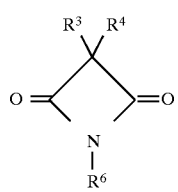    ID wherein both dotted lines represent optional double bonds;

m is an integer from zero to four;

Z is oxygen or sulfur when it is double bonded to ring A and Z is hydroxy, ($C_1$-$C_{10}$) alkyl-S-,adamant-2-yl-S-, benzyl-S-,phenyl-C(=O)$CH_2$-S-, ($C_{1-C_6}$)alkyl—O—C (=O)$CH_2$—S—or (H, H) when Z is single bonded to ring A;

X is $CH_2CH_2$, NR$^1$, CHR$^1$ or a direct link between the carbon to which Z is attached and the carbon to which R$^3$ and R$^4$ are attached;

R$^2$ and R$^6$ are independently selected from naphthyl, phenyl, ($C_1$–$C_6$)alkylphenyl, 1-adamantyl, 2-adamantyl, ($C_1$–$C_8$) straight or branched alkyl, ($C_3$–$C_{10}$) cycloalkyl and ($C_8$–$C_{30}$)bicyclic or tricyclic alkyl; wherein said ($C_3$–$C_{10}$)cycloalkyl and said ($C_8$–$C_{30}$) bicyclic or tricyclic alkyl may optionally be substituted with a hydroxy group; and wherein said adamantyl groups may optionally be substituted with from one to three substituents independently selected from ($C_1$–$C_6$)alkyl, halo and hydroxy;

R$^3$ and R$^4$ are independently selected from benzyl, wherein the phenyl moiety of said benzyl may optionally be substituted with an amino or nitro group; hydrogen, phenyl, (N≡C)-($C_1$–$C_6$)alkyl, ($C_1$–$C_6$) alkyl—O—C(=O)-($C_1$–$C_6$)alkyl and Het-$CH_2$,wherein Het is selected from 2-, 3- or 4-pyridinyl, furyl, tetrahydrofuryl, pyrimidyl, pyrazinyl, pyrazolyl, isoxazolyl, thiophenyl and triazolyl;

R$^5$ is hydrogen, phenyl-($C_1$–$C_6$)alkyl, ($C_1$–$C_{10}$)alkyl or ($C_1$–$C_6$)alkyl—C(=O)—;

W is hydrogen, $OR^7$, hydroxy, $R^{11}$ or $NR^{12}R^{13}$;

each of $R^7$ and $R^{11}$ is independently selected from $(C_1-C_3)$alkyl;

each of $R^{12}$ and $R^{13}$ is independently selected from $(C_1-C_3)$alkyl; and $R^{14}$ is hydrogen, $(C_1-C_4)$alkyl, benzyl or phenyl;

with the proviso that (a) no more than one of the two dotted lines in formula IA can represent a double bond in any one compound, (b) when Z is (H, H), X is $CH_2$ or $CH_2CH_2$, (c) when Z is oxygen or (H, H) and X is $CHR^1$, $R^1$ must be hydrogen, (d) when Z is sulfur and X is $NR^1$, $R^1$ must be hydrogen, and (e) one of $R^3$ and $R^4$ must be Het-$CH_2$;

or a pharmaceutically acceptable salt of such compound.

2. A compound according to claim 1 having the formula IA and wherein X is $CH_2$, Z is oxo and $R^2$ is 1- or 2-adamantyl.

3. A compound according to claim 1 having the formula IA wherein $R^2$ is 1- or 2-adamantyl.

4. A compound according to claim 1 having the formula IA wherein $R^2$ is $(C_3-C_{10})$ cycloalkyl.

5. A compound according to claim 1 having the formula IB wherein $R^6$ is 1-adamantyl or 2-adamantyl.

6. A compound according to claim 1 having the formula IB wherein $R^6$ is $(C_3-C_{10})$ cycloalkyl.

7. A compound according to claim 1 having the formula IA wherein X is $CH_2$.

8. A compound according to claim 1 having the formula IA wherein Z is (H, H).

9. A compound according to claim 7 wherein Z is (H, H).

10. A compound according to claim 1 having the formula IA wherein Z is oxygen.

11. A compound according to claim 1 having the formula IA wherein Z is sulfur.

12. A compound according to claim 11 wherein X is NH.

13. A compound according to claim 1 having the formula IB wherein $R^5$ is hydrogen.

14. A compound according to claim 1 having the formula IB wherein $R^5$ is $(C_1-C_6)$alkyl.

15. A compound according to claim 1 having the formula IB wherein $R^5$ is $(C_1-C_6)$alkyl—C(=O)—.

16. A compound according to claim 1 having the formula IA wherein one or both of $R^3$ and $R^4$ are selected from 2-, 3- and 4-pyridinylmethyl.

17. A compound according to claim 1 wherein one of $R^3$ and $R^4$ is 2- or 3-furyl.

18. A compound according to claim 1 wherein one of $R^3$ and $R^4$ is (N≡C)-$(C_1-C_6)$alkyl.

19. A compound according to claim 1 wherein one of $R^3$ and $R^4$ is $(C_1-C_6)$alkyl—O—C(=O)-$(C_1-C_6)$alkyl.

20. A compound according to claim 1 wherein one of $R^3$ and $R^4$ is 1- or 2-triazolyl.

21. A compound according to claim 1 having the formula IA wherein Z is other than hydroxy.

22. A compound according to claim 1 having the formula IA wherein X is $NR^1$ and $R^1$ is present or absent.

23. A compound according to claim 1 having the formula IA, IB, IC or ID and wherein $R^3$ and $R^4$ are independently selected from Het-$CH_2$.

24. A compound according to claim 1 having the formula IB wherein one of $R^3$ and $R^4$ is 2-, 3- or 4-pyridinylmethyl.

25. A compound according to claim 1 wherein $R^2$ or $R^6$ is selected from $(C_8-C_{30})$ bicyclic or tricyclic alkyl.

26. A compound according to claim 1 having the formula IC wherein W is $OR^7$.

27. A compound according to claim 1 having the formula IC wherein W is $(C_1-C_6)$alkyl.

28. A compound of the formula IB wherein $R^{14}$ is hydrogen.

29. A compound according to claim 1 having the formula IC or ID wherein one or both of $R^3$ and $R^4$ are 2-, 3- or 4-pyridinylmethyl.

30. A pharmaceutical composition for treating Alzheimer's disease, age associated memory impairment or Parkinson's disease in a human, comprising an amount of a compound according to claim 1 that is effective in treating such condition, and a pharmaceutical acceptable carrier.

31. A method of treating Alzheimer's disease, age associated memory impairment or Parkinson's disease in a human, comprising administering to said human an amount of a compound according to claim 1 that is effective in treating such condition.

32. A pharmaceutical composition for treating Alzheimer's disease, age associated memory impairment or Parkinson's disease in a human, comprising an acetylcholine release enhancing effective amount of a compound according to claim 1 and a pharmaceutically acceptable carrier.

33. A method of treating Alzheimer's disease, age associated memory impairment or Parkinson's disease in a human, comprising an administering to said human an acetylcholine, dopamine or serotonin release enhancing effective amount of a compound according to claim 1.

34. A pharmaceutical composition for treating a disease or condition, the treatment of which can be effected or facilitated by enhancing acetylcholine, dopamine or serotonin release in a human, comprising an acetylcholine, dopamine or serotonin release enhancing effective amount of a compound according to claim 1 and a pharmaceutically acceptable carrier.

35. A method of treating a disease or condition, the treatment or prevention of which can be effected or facilitated by enhancing acetylcholine release in a human, comprising administering to said human an acetylcholine, dopamine or serotonin release enhancing effective amount of a compound according to claim 1.

36. A pharmaceutical composition for treating a condition selected from mental retardation, developmental disorders, disruptive behavioral disorders, organic mental disorders, psychoactive substance abuse disorders, mood disorders, anxiety disorders, somatoform disorders, dissociative disorders, attention deficit disorder, schizophrenia and personality disorders in a human, comprising an amount of a compound according to claim 1 that is effective in treating such condition, and a pharmaceutical acceptable carrier.

37. A method of treating a condition selected from mental retardation, developmental disorders, disruptive behavioral disorders, organic mental disorders, psychoactive substance abuse disorders, mood disorders, anxiety disorders, somatoform disorders, dissociative disorders, attention deficit disorder, schizophrenia and personality disorders in a human, comprising administering to said human an amount of a compound according to claim 1 that is effective in treating such condition.

38. A pharmaceutical composition for treating a condition selected from mental retardation, developmental disorders, disruptive behavioral disorders, organic mental disorders, psychoactive substance abuse disorders, mood disorders, anxiety disorders, somatoform disorders, dissociative disorders, attention deficit disorder, schizophrenia and personality disorders in a human, comprising an acetylcholine, dopamine or serotonin release enhancing effective amount of a compound according to claim 1 and a pharmaceutically acceptable carrier.

39. A method of treating a condition selected from mental retardation, developmental disorders, disruptive behavioral disorders, organic mental disorders, psychoactive substance abuse disorders, mood disorders, anxiety disorders, somatoform disorders, dissociative disorders, attention deficit disorder, schizophrenia and personality disorders in a human, comprising an administering to said human an acetylcholine, dopamine or serotonin release enhancing effective amount of a compound according to claim 1.

40. A pharmaceutical composition for the treatment of Alzheimer's disease, age associated memory impairment or Parkinson's disease in a human, comprising an acetylcholine release enhancing effective amount of a compound according to claim 1, an acetylcholine esterase inhibiting effective amount of an acetylcholine esterase inhibitor or a pharmaceutically acceptable salt thereof, and a pharmaceutically acceptable carrier.

41. A method of treating Alzheimer's disease, age associated memory impairment or Parkinson's disease in a human, comprising administering to said human an acetylcholine release enhancing effective amount of a compound according to claim 1 in combination with an acetylcholine esterase inhibiting effective amount of an acetylcholine esterase inhibitor or a pharmaceutically acceptable salt thereof.

42. A pharmaceutical composition for the treatment of a condition selected from mental retardation, developmental disorders, disruptive behavioral disorders, organic mental disorders, psychoactive substance abuse disorders, mood disorders, anxiety disorders, somatoform disorders, dissociative disorders, attention deficit disorder, schizophrenia and personality disorders in a human, comprising an acetylcholine release enhancing effective amount of a compound according to claim 1 in combination with an acetylcholine esterase inhibiting effective amount of an acetylcholine esterase inhibitor or a pharmaceutically acceptable salt thereof, and a pharmaceutically acceptable carrier.

43. A method of treating a condition selected from mental retardation, developmental disorders, disruptive behavioral disorders, organic mental disorders, psychoactive substance abuse disorders, mood disorders, anxiety disorders, somatoform disorders, dissociative disorders, attention deficit disorder, schizophrenia and personality disorders in a human, comprising administering to said human an acetylcholine release enhancing effective amount of a compound according to claim 1 in combination with an acetylcholine esterase inhibiting effective amount of an acetylcholine esterase inhibitor or a pharmaceutically acceptable salt thereof.

\* \* \* \* \*